(12) United States Patent
Chan et al.

(10) Patent No.: US 8,765,443 B2
(45) Date of Patent: Jul. 1, 2014

(54) CRYSTALS OF HUMAN TOPOISOMERASE II-DNA BINARY COMPLEX, METHODS FOR PREPARING THE SAME AND USES THEREOF

(75) Inventors: Nei-Li Chan, Taipei (TW); Tsai-Kun Li, Taipei (TW); Chyuan-Chuan Wu, Taipei (TW); Ying-Ren Wang, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 13/556,687

(22) Filed: Jul. 24, 2012

(65) Prior Publication Data

US 2013/0018180 A1  Jan. 17, 2013

Related U.S. Application Data

(63) Continuation-in-part of application No. 13/527,960, filed on Jun. 20, 2012, now abandoned.

(60) Provisional application No. 61/498,621, filed on Jun. 20, 2011.

(51) Int. Cl.
| | | |
|---|---|---|
| C07H 21/04 | (2006.01) | |
| C12N 9/90 | (2006.01) | |
| C07H 15/252 | (2006.01) | |
| G01N 23/20 | (2006.01) | |

(52) U.S. Cl.
CPC ........... *C12Y 599/01003* (2013.01); *C12N 9/90* (2013.01); *C07K 2299/00* (2013.01)
USPC ............ 435/233; 536/18.1; 536/23.1; 436/94

(58) Field of Classification Search
CPC ......................... C12Y 599/01003; C12N 9/90; C07K 2299/00
USPC .................... 536/18.1, 23.1; 435/233; 436/94
See application file for complete search history.

(56) References Cited

FOREIGN PATENT DOCUMENTS

WO    WO2008154432    * 12/2008

* cited by examiner

*Primary Examiner* — Brandon Fetterolf
*Assistant Examiner* — Yih-Horng Shiao
(74) *Attorney, Agent, or Firm* — Bacon & Thomas, PLLC

(57) ABSTRACT

Disclosed herein are a crystal of a human TOPII (hTOPII)-DNA binary complex, the method for preparing the same and the use thereof. The hTOPII-DNA binary complex includes an hTOPII portion that contains an hTOPII core domain (hTOPII$^{core}$), and a synthetic double-stranded DNA in complex with the hTOPII portion. The synthetic double-stranded DNA has a first DNA strand comprising nucleotide positions 3 to 20 of the sequence of 5'-NNNCCGAGCNNNNGCTCG-GNNN-3' (SEQ ID NO: 1), wherein N is any one of adenine, thymine, cytosine, or guanine, and a second DNA strand complementary to the first DNA strand.

35 Claims, 24 Drawing Sheets
(23 of 24 Drawing Sheet(s) Filed in Color)

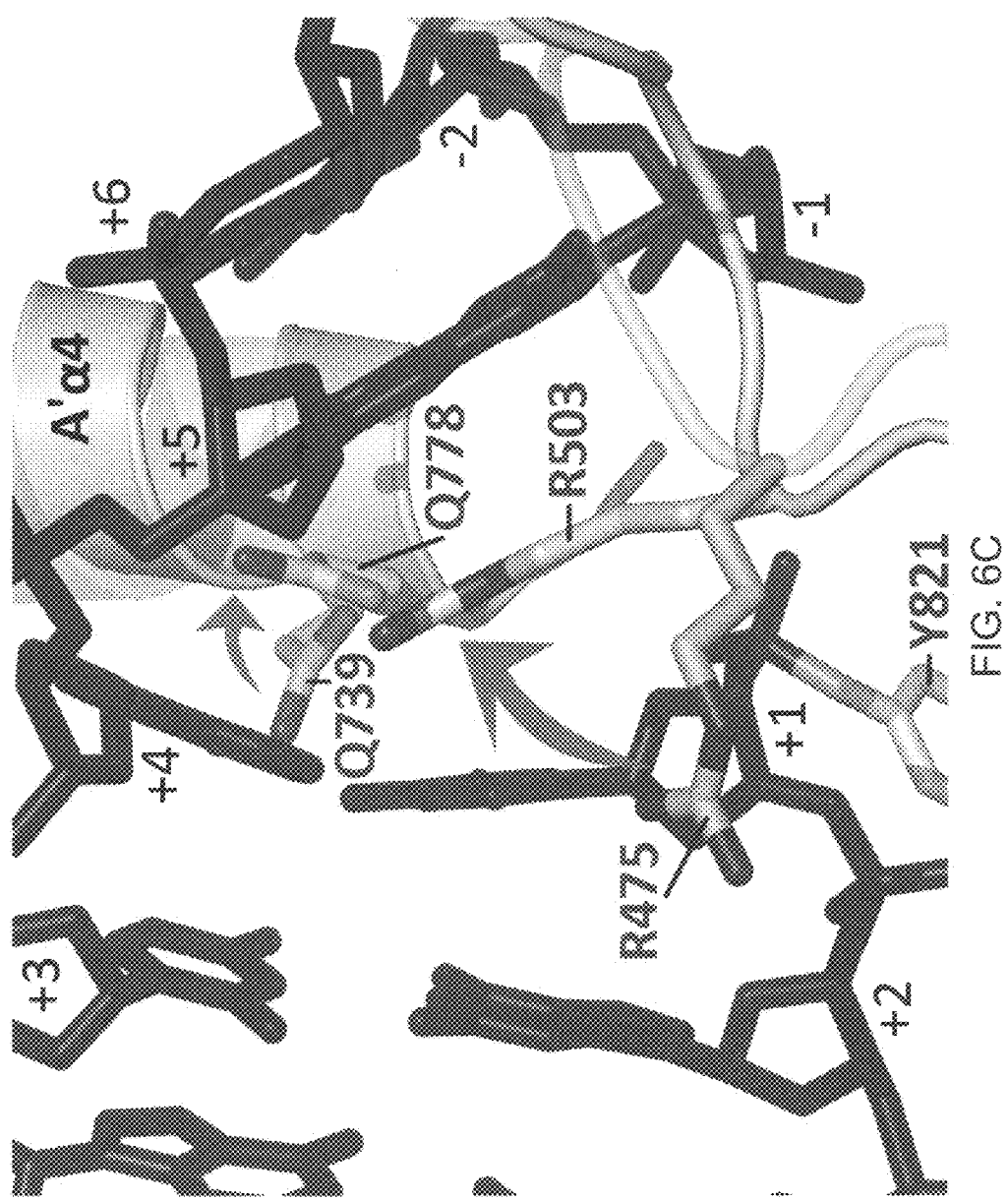

SEQUENCE LISTING

<160> NUMBER OF SEQ ID NOS: 3

<210> SEQ ID NO 1

```
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t
<220> FEATURE:
<221> NAME/KEY: misc_feature
<222> LOCATION: (20)..(22)
<223> OTHER INFORMATION: n is a, c, g, or t

<400> SEQUENCE: 1
nnnccgagcn nnngctcggn nn                                              22

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
gccgagctgc agctcggc                                                   18

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
agccgagctg cagctcggct                                                 20
```

CRYSTALS OF HUMAN TOPOISOMERASE II-DNA BINARY COMPLEX, METHODS FOR PREPARING THE SAME AND USES THEREOF

BACKGROUND OF THE INVENTION

1. Field of the Invention

The present disclosure relates to a crystal structure of a protein-DNA binary complex. More particularly, the disclosure relates to the crystal structure of a human topoisomerase II (hTOPII)-DNA binary complex and its uses for identifying candidate compounds exhibiting inhibitory effects toward hTOPII, specifically, the cc and (3 form of hTOPII.

2. Description of Related Art

DNA topoisomerases (TOPs) are enzymes that change DNA topology by catalyzing the passage of DNA strands across each other. There are two well-characterized classes of topoisomerases, type I topoisomerase (TOPI) and type II topoisomerase (TOPII). TOPI acts by breaking and religating one DNA strand, while TOPII involves double-strand breaking. These enzymes play key roles in DNA replication, transcription, and recombinant repair. In particular, TOPII is highly expressed in rapidly proliferating cells and is therefore an attractive target for the development of antitumor drugs.

TOPIIs are two-fold symmetric enzymes that alter DNA topology by transiently cleaving a pair of opposing phosphodiester bonds four base pairs apart via the formation of two reversible 5'-phosphotyrosyl linkages, thereby generating a TOPII-DNA cleavage complex that harbors a double-stranded DNA break. Under physiological conditions, these TOPII-DNA cleavage complexes are normally short lived intermediates in the catalytic cycle of the enzyme. Passage of a second DNA segment through this TOPII-DNA cleavage complex and its resealing complete the topological change of the DNA. The DNA cleavage activity of TOPII is known as a double-edged sword; failure to reseal the enzyme-mediated DNA break can lead to permanent DNA damage followed by cell death.

There are two general classes of TOPII-targeting drugs: TOPII poisons and TOPII catalytic inhibitors. TOP II poisons include etoposide (VP-16), doxorubicin, amsacrine (mAMSA) and mitoxantrone. These compounds serve to stabilize the TOPII-DNA cleavage complex thereby increasing the steady-state levels of cleavage complexes. Hence TOPII poisons convert TOPII into a physiological toxin that creates DNA double-strand breaks in the genome of treated cells. The catalytic inhibitors, on the other hand, block the catalytic activity of DNA-TOPII cleavage complex by preventing the binding of the enzyme to DNA rather than stabilizing the DNA-TOPII cleavage complex. Examples of catalytic TOPII inhibitors include novobiocin, dexrazoxane (ICRF-187) and GSK 299423.

Crystallography is a powerful tool for investigating the interactions among protein, DNA, and drugs. In this disclosure, crystal structures of the DNA-binding and cleavage core of hTOPII (hTOPII core domain; hTOPII$^{core}$) in complexes with DNA and antitumor drugs were used to obtain high resolution and homogeneous crystal structure of binary TOPII$^{core}$-DNA cleavage complex, which is useful for constructing a high throughput screening platform for identifying candidate compounds having inhibitory effects toward hTOPII. As such, potential lead compound having anti-tumor effects may be identified and subsequently being developed into an anti-neoplastic medicine.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a synthetic double-stranded DNA for forming an hTOPII$^{core}$-DNA binary complex. The sequence of this synthetic double-stranded DNA is designed to facilitate drug-induced cleavage at specific positions so as to ensure homogeneity of the complexes produced.

According to one embodiment of the present disclosure, the double-stranded DNA has a first DNA strand comprising the sequence from 5' to 3', NNCCGAGCNNNNGCTCG-GNN, wherein N is any one of adenine (A), thymine (T), cytosine (C) or guanine (G); and a second DNA strand that is complementary to the first DNA strand.

In another aspect, the present invention is directed to a method for preparing a crystal of an hTOPII$^{core}$-DNA binary complex. The thus-obtained crystals are high resolution crystal structures suitable for use in crystallographic studies to obtain structural data thereof.

According to one embodiment of the present invention, the method comprises the steps as follows. An hTOPII portion comprising an hTOPII core domain (hTOPII$^{core}$), a synthetic double-stranded DNA as described in other aspect/embodiment(s) of the present disclosure, and a ligand are mixed to form an hTOPII$^{core}$-DNA-ligand ternary complex. Afterwards, the hTOPII-DNA-ligand complex is mixed with a first solution to crystallize the hTOPII$^{core}$-DNA-ligand ternary complex. The ligand is then soaked out from the crystallized hTOPII$^{core}$-DNA-ligand ternary complex by placing the crystallized hTOPII$^{core}$-DNA-ligand ternary complex in a second solution to obtain the crystal of the hTOPII$^{core}$-DNA binary complex. The first solution includes 100 mM magnesium acetate, 50 mM 2-(N-morpholino)ethanesulfonic acid (pH 5.6-6.5; preferably, pH 5.8), and 18-22 wt % 2-methyl-1,6-hexanediol (MPD). The second solution has the same composition as that of the first solution except the concentration of MPD is greater than that of the first solution. For example, the second solution may comprise about 20-40% (wt %) MPD. In one embodiment, the first solution comprises about 22 wt % MPD, whereas the second solution comprises about 30 wt % MPD.

In still another aspect, the present disclosure is directed to a crystal of an hTOPII$^{core}$-DNA binary complex. The three dimensional structure obtained from this crystal of the hTOPII$^{core}$-DNA binary complex provides the structural basis of the interaction between hTOPII and DNA. Also, the crystal of an hTOPII$^{core}$-DNA binary complex serves as a platform for investigating interactions among hTOPII, the DNA, and the ligand (such as anticancer drugs) in an hTOPII$^{core}$-DNA-ligand ternary complex. Moreover, this crystal of the hTOPII$^{core}$-DNA binary complex could be used in a high throughput screening platform for identifying a candidate compound exhibiting inhibitory effect towards the hTOPII.

According to one embodiment of the present disclosure, the crystal of an hTOPII$^{core}$-DNA binary complex comprises: (1) an hTOPII portion comprising an MPH core domain (hTOPII$^{core}$); and (2) a synthetic double-stranded DNA in complex with the hTOPII portion, wherein the synthetic double-stranded DNA has a first DNA strand of 5'-NNC-CGAGCNNNNGCTCGGNN-3', wherein N is any one of A, T, C, or G, and a second DNA strand that is complementary to the first DNA strand.

In yet another aspect, the present invention is directed to a crystal of an hTOPII$^{core}$-DNA-ligand ternary complex useful for the method of this disclosure to obtain the hTOPII$^{core}$-DNA binary complex.

According to one embodiment of the present invention, the crystal of the hTOPII$^{core}$-DNA-ligand ternary complex comprises: (1) an hTOPII portion comprising an hTOPII core domain (hTOPII$^{core}$); (2) a synthetic double-stranded DNA in complex with the hTOPII portion, wherein the synthetic double-stranded DNA has a first DNA strand of 5'-NNC-CGAGCNNNNGCTCGGNN-3', wherein N is any one of A, T, C, or G, and a second DNA strand that is complementary to the first DNA strand; and (3) a ligand; wherein both the synthetic double-stranded DNA and the ligand are in complex with the hTOPII portion.

In still another aspect, the present invention is directed to a high throughput screening platform for identifying a ligand which is a hTOPII-targeting agent exhibiting inhibitory effect towards the hTOPII, According to one embodiment of the present invention, the high throughput screening platform comprises forming an hTOPII$^{core}$-DNA-ligand ternary complex by soaking a ligand into the crystal of hTOPII$^{core}$-DNA binary complex; obtaining X-ray crystal diffraction patterns of the hTOPII$^{core}$-DNA-ligand ternary complex; and using the X-ray crystal diffraction pattern to analyze the structure of hTOPII$^{core}$-DNA-ligand ternary complex, and identify ligand-interacting residues on hTOPII.

In another one aspect, the present invention is directed to an hTOPII-targeting agent for enhancing stability and specificity toward the DNA cleavage site and mediating hTOPII-specific interactions.

According to one embodiment of the present invention, the hTOPII-targeting agent comprises a core domain of polycyclic ring system inserting into a DNA cleavage site, wherein the polycyclic ring system has a number of cyclic rings are 2, 3, or 4, and the individual ring is aromatic or non-aromatic.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where:

FIG. 6C illustrates that residues Arg503 and Gln778 show different side chain conformations in the drug-free hTOPIIβ and yeast TOPII structures. Insertion of residues Arg503 and Gln778 into the cleavage sites was observed in the structure of drug-free hTOPIIβ$^{core}$-DNA binary complex.

DESCRIPTION

Figure 1B:
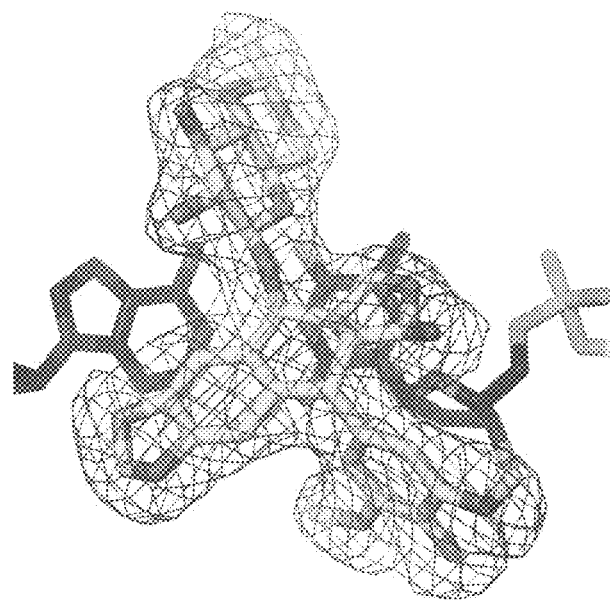
FIGS. 1A to 1F are electron density maps of the drug-binding sites and the bound etoposide (FIGS. 1A and 1B), mitoxantrone (FIGS. 1C and 1D), and doxorubicin (FIGS. 1E and 1F) in respective drug-stabilized hTOPIIβ$^{core}$-DNA ternary complexes.
Figure 1A:
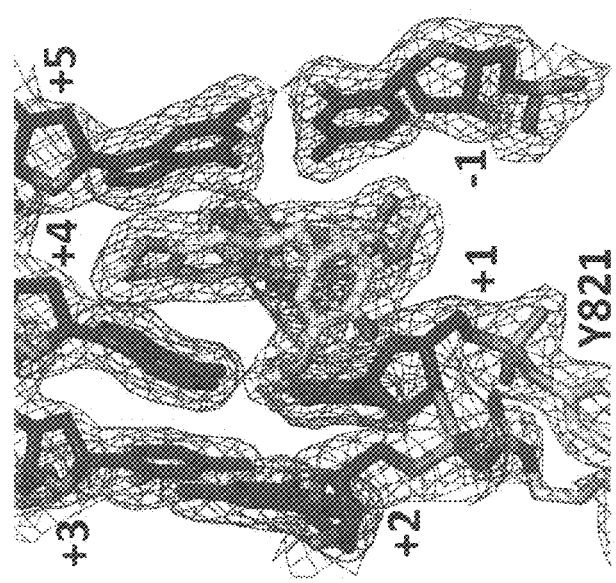
Figure 1D:
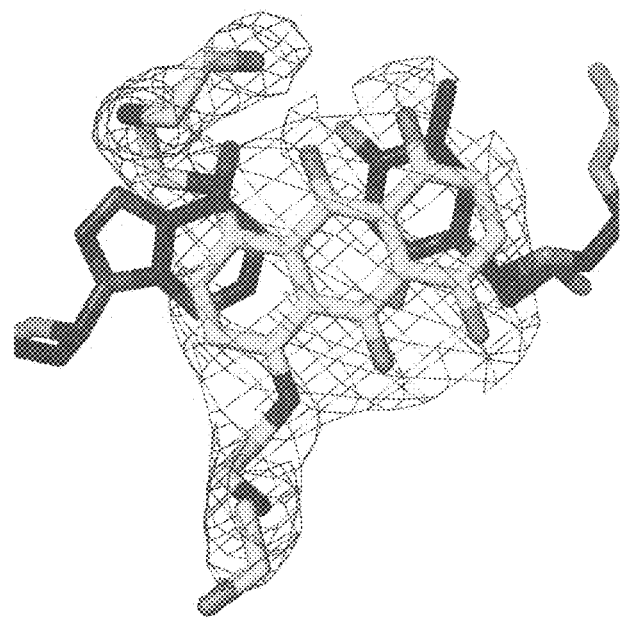
Figure 1C:
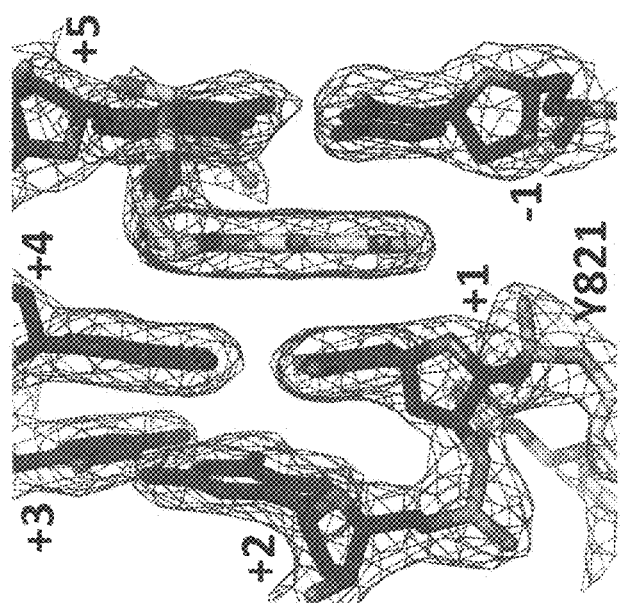

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless defined otherwise, all technical and scientific terms used herein have the same meaning as commonly understood by one of the ordinary skill in the art to which this invention belongs.

The singular forms "a", "and", and "the" are used herein to include plural referents unless the context clearly dictates otherwise.

The term "crystal" refers to an ordered state of matter. As could be appreciated by those with ordinary skills in the art, proteins, by their nature are difficult to purify to homogeneity. Regarding crystals of protein-DNA binary complexes, the situation is more complicated since a number of factors may affect the positions at which the protein interacts with the DNA. The term "mature crystals" refer to crystals with sufficient order allowing X-ray diffraction. As could be appreciated by persons with ordinary skills in the art, some crystals diffract better than others. Generally, crystals useful for X-ray analysis are typically single, 0.05 mm or larger, and free of cracks and defects. However, advances in technology allow increasingly smaller crystals to be analyzed.

The term "ligand" describes a compound that binds to the hTOPII molecule or the binary complex of hTOPII and DNA. The ligand bound binary complex is termed "ternary complex" in the present disclosure. In preferred embodiments of the present disclosure, the ligands are TOPII-targeting agents may serve as anticancer drugs.

Objective of this invention aims at providing crystals of hTOPII$^{core}$-DNA binary complex useful in a high throughput screening platform for identifying a candidate compound exhibiting inhibitory effect towards hTOPII. As known by those with ordinary skills in the art, natural occurring hTOPII$^{core}$-DNA binary complexes are only formed transiently in the catalytic cycle of hTOPII, which renders it difficult to obtain crystals directly from the natural occurring hTOPII$^{core}$-DNA binary complexes. Inventors of the present disclosure address this obstacle by first creating crystals of hTOPII$^{core}$-DNA-ligand ternary complex using a novel, synthetic double-stranded DNA as the substrate of hTOPII, and an anticancer drug as the ligand; and then proceed to obtain crystals of hTOPII$^{core}$-DNA binary complex by soaking out the bound ligand. The thus obtained hTOPII$^{core}$-DNA binary complexes may then be used to construct a high throughput screening platform for identifying potential candidates, which are hTOPII-targeting agents.

As could be appreciated by those with ordinary skills in the art, preferred nucleotide sequences for drug-induced cleavage by the hTOPII-DNA cleavage complex vary from one drug to another. As such, in one aspect of the present disclosure, a novel, synthetic double-stranded DNA is designed to facilitate drug-induced cleavage at specific positions so as to ensure homogeneity of the produced hTOPII-DNA complexes.

In general, the design of the nucleotide sequence is based on the cleavage pattern of TOPII, after being treated with various anticancer drugs, including etoposide (VP-16), teniposide (VM-26), and mitoxantrone. The thus designed double-stranded DNA can then be synthesized by any conventional DNA synthesis methods and/or commercially available kits for DNA synthesis.

Inventors of this invention found that the synthetic double-stranded DNA suitable for the purpose of this invention preferably has 18 to 22 nucleotides in length; more preferably has 20 nucleotides in length. Further, nucleotides at some positions may be varied, whereas nucleotides at other positions should always remain the same. The novel, synthetic double-stranded DNA of this disclosure may have a first DNA strand corresponding to nucleotide positions 3 to 20 of the sequence of 5'-NNNCCGAGCNNNNGCTCGGNNN-3' (SEQ ID NO: 1), wherein N is any one of adenine (A), thymine (T), cytosine (C) or guanine (G); and a second DNA strand that is complementary to the first DNA strand. The present synthetic DNA contains a preferred 5'-C↓NNNNG-3' cleavage site, which corresponds to nucleotide positions 9 to 14 of SEQ ID NO:1, so as to encourage the formation of drug-stabilized DNA scission at specific positions, in which the arrow indicates the cleavage position where the synthetic DNA is cut by hTOPII.

In one example described in the present disclosure, the first DNA strand has a sequence from 5' to 3', GCCGAGCTG-CAGCTCGGC (SEQ ID NO: 2, which corresponds to nucleotide sequence positions 3-20 of SEQ ID NO: 1). Other DNA sequences suitable for use herein include 5'-AGCCGAGCT-GCAGCTCGGCT-3' (SEQ ID NO: 3, which corresponds to nucleotide sequence positions 2-21 of SEQ ID NO: 1). In these examples, the 5' to 3' nucleotide sequence on the 5' side of the preferred 5'-C↓NNNNG-3' cleavage site is complementary to the 3' to 5' nucleotide sequence on the 3' side of the preferred cleavage site, in which the arrow indicates the cleavage position where the synthetic DNA is cut by hTOPII. Take SEQ ID NO: 2 and SEQ ID NO: 3 as examples, the 5' to 3' nucleotide sequence, 5'-C↓TGCAG-3', on the 5' side of the preferred cleavage site, is complementary to the sequence 3'-G↓ACGTC-5' on the 3' side of the preferred cleavage site, in which the arrow indicates the cleavage position where the synthetic DNA is cut by hTOPII.

Preferably, the hTOPII comprises α form and β form.

The present invention also relates to a method for obtaining a crystal of an hTOPII$^{core}$-DNA binary complex. The method includes steps of:

(a) forming an hTOPII$^{core}$-DNA-ligand ternary complex by mixing an hTOPII portion comprising an hTOPII core domain (hTOPII$^{core}$), a synthetic double-stranded DNA as described above, and a ligand;

(b) crystallizing the hTOPII$^{core}$-DNA-ligand ternary complex by mixing the hTOPII$^{core}$-DNA-ligand ternary complex with a reservoir solution; and (c) soaking out the ligand from the crystallized hTOPII$^{core}$-DNA-ligand ternary complex by placing the crystallized hTOPII$^{core}$-DNA-ligand ternary complex in a fresh reservoir solution comprising MPD in an amount that is greater than that in the reservoir solution of step (b) and thereby obtaining the crystal of the hTOPII$^{core}$-DNA binary complex.

In order to obtain suitable crystals of binary complex, the hTOPII portion may be expressed recombinantly in bacteria, insect cell cultures, or mammalian cell cultures, and then purified via standard procedures.

Human cells express two isozymes, hTOPII-alpha (hTOPIIα) and hTOPII-beta (hTOPIIβ) with distinct biological regulations at the levels of gene expression and cellular locations. Also, the synthetic double-stranded DNA having a first DNA strand of 5'-AGCCGAGCTGCAGCTCGGCT-3' (SEQ ID NO: 3) is used in the example to ensure the homogeneity of the crystals. The ligand used in the example to create hTOPII$^{core}$-DNA-ligand ternary complexes are etoposide or mitoxantrone. In the present case, the hTOPII portion is mixed with 2 mM ligands, and the synthetic double-stranded DNA; in which the molar ratio of the synthetic double-stranded DNA to the hTOPII portion is about 1:1 to 1.5:1. According to one example, the molar ratio is about 1.2:1.

In one example, when forming an hTOPII$^{core}$-DNA-ligand ternary complex, the hTOPII can be hTOPIIα and the first DNA strand has a sequence from 5' to 3' AGCCGAGCTG-CAGCTCGGCT (SEQ ID NO: 3); the ligand is mitoxantrone. The molar ratio of the synthetic double-stranded DNA to the hTOPIIα, portion is also the same as the ratio described above.

Preferably, crystals of hTOPIIα$^{core}$-DNA-mitoxantrone ternary complex can be grown, for example, by the hanging drop or sitting drop vapor diffusion method in the reservoir solution described above comprises 100 mM magnesium acetate, 50 mM 2-(N-morpholino)ethanesulfonic acid (pH 5.2-6.0), and 20-27 wt % 2-methyl-1,6-hexanediol (MPD).

Mature crystals suitable for crystallographic data collection usually appear within several months.

To obtain crystals of the hTOPIIα$^{core}$-DNA binary complexes, the ternary complexes are soaked in a fresh reservoir solution, which comprises the same composition as the reservoir solution except having 30-40 wt % MPD to remove the mitoxantrone. This step may take 10, 11, 12, 13, 14, 15, 16, 17, 18, 19, 20, 21, 22, 23, or sometimes up to 24 hours.

When forming an hTOPII$^{core}$-DNA-ligand ternary complex, the hTOP II can be hTOPIIβ, and the first DNA strand has a sequence from 5' to 3' AGCCGAGCTGCAGCTCG-GCT (SEQ ID NO: 3); the ligand is etoposide, which is dissolved in dimethyl sulfoxide (DMSO).

Preferably, crystals of hTOPIIβ$^{core}$-DNA-etoposide ternary complexes can be grown, for example, by the hanging drop or sitting drop vapor diffusion method in the reservoir solution described above comprises 100 mM magnesium acetate, 50 mM 2-(N-morpholino)ethanesulfonic acid (pH 5.6-6.5), and 18-22 wt % 2-methyl-1,6-hexanediol (MPD). Mature crystals suitable for crystallographic data collection usually appear within a week.

To obtain crystals of the hTOPIIβ$^{core}$-DNA binary complexes, the ternary complexes are soaked in a fresh reservoir solution, which comprises the same composition as the reservoir solution except having 20-40 wt % MPD to remove the etoposide. This step may take 10, 11, 12, 13, 14, 15, 16, 17, 18, 19, 20, 21, 22, 23, or sometimes up to 24 hours. The harvested crystals of hTOPIIβ$^{core}$-DNA binary complexes are then looped and flash-frozen in liquid nitrogen for data collection.

The present disclosure also relates to a crystal obtainable by the methods of the present invention. The three dimensional structure obtained from this crystal provides the structural basis of the interaction between hTOPII and the DNA.

According to one embodiment of the present disclosure, the crystal of an hTOPII$^{core}$-DNA binary complex comprises: (1) an hTOPII portion comprising an hTOPII core domain (hTOPII$^{core}$), and (2) a synthetic double-stranded DNA in complex with the hTOPII portion, wherein the synthetic double-stranded DNA has a first DNA strand corresponding to nucleotide positions 3 to 20 of the sequence of 5'-NNNC-CGAGCNNNNGCTCGGNNN-3' (SEQ ID NO: 1), wherein N is any one of A, T, C, or G; and a second DNA strand that is complementary to the first DNA strand.

In one example, the hTOPII is hTOPIIα, and the first DNA strand has a sequence from 5' to 3', AGCCGAGCTG-CAGCTCGGCT (SEQ ID NO: 3). In this case, the ligand is mitoxantrone, and the crystal of hTOPIIα$^{core}$-DNA-mitoxantrone ternary complex has a crystal lattice in a P2$_1$22$_1$ space group and unit cell dimensions of a=105.4±2 Å, b=126.2±3 Å, and c=198.0±2 Å.

In another example, the hTOPII is hTOPII-beta, and the first DNA strand has a sequence from 5' to 3', AGCCGAGCT-GCAGCTCGGCT (SEQ ID NO: 3). In this case, the crystal of hTOPIIβ$^{core}$-DNA-etoposide ternary complex has a crystal lattice in a P2$_1$ space group and unit cell dimensions of a=80.0±2.0 Å, b=176.4±3 Å, c=94.2±2 Å, and β=112.1±3 degree.

The present disclosure also relates to crystals of hTOPII-DNA-ligand ternary complexes. According to principles and spirits of the present invention, the ligand could be any anticancer drug known to exhibit inhibitory effect toward hTOPII, and the crystals of the ternary complex is suitable for X-ray diffraction. As such, the diffraction data collected from crystals containing various ligands may help elucidate the interaction among hTOPII, DNA and these ligands, which in turn, may be helpful in designing future antitumor drugs with improved efficacy and less undesired side effects.

According to embodiments of the present disclosure, these crystals of hTOPII$^{core}$-DNA-ligand ternary complexes could be obtained by adding the ligand to the drop containing the crystals of hTOPII$^{core}$-DNA binary complexes described hereinabove, and allow the structural determination of the ternary complexes to proceed.

According to one embodiment of the present invention, the crystal of the hTOPII$^{core}$-DNA-ligand ternary complex comprises: (1) an hTOPII portion comprising an hTOPII core domain (hTOPII$^{core}$), (2) a synthetic double-stranded DNA in complex with the hTOPII portion, wherein the synthetic double-stranded DNA has a first DNA strand corresponding to nucleotide positions 3 to 20 of the sequence of 5'-NNNC-CGAGCNNNNGCTCGGNNN-3' (SEQ ID NO: 1), wherein N is any one of A, T, C, or G; and a second DNA strand that is complementary to the first DNA strand, and (3) a ligand, wherein both the synthetic double-stranded DNA and the ligand are in complex with the hTOPII portion.

Ligands suitable for use herein include, but are not limited to, epipodophyllotoxins such as etoposide (VP-16), podophyllotoxin (PPT) or teniposide (VM-26); anthracenediones such as mitoxantrone, pixantrone, or ametantrone; anthracyclines such as doxorubicin, daunorubicin, epirubicin, aclarubicin or idarubicin; acridines such as amsacrine (mAMSA), AMCA, mAMCA or DACA.

According to some examples of the present disclosure, the hTOPII is hTOPIIβ, and the first DNA strand has a sequence from 5' to 3', AGCCGAGCTGCAGCTCGGCT (SEQ ID NO: 3). In one example, the ligand is mitoxantrone, and the crystal has a crystal lattice in a P2$_1$ space group and unit cell dimensions of a=80.5±2 Å, b=176.6±3 Å, c=93.8±2 Å, and =111.5±3 degree. In still another example, the ligand is doxorubicin, and the crystal has a crystal lattice in a P2$_1$ space group and unit cell dimensions of a=80.3±2 Å, b=176.6±3 Å, c=94.0±2 Å, and 0=111.5±3 degree. In one another example, the ligand is amsacrine, and the crystal has a crystal lattice in a P2$_1$ space group and unit cell dimensions of a=80.2±2 Å, b=176.8±3 Å, c=94.0±3 Å, and β=111.6±3 degree. In further another example, the ligand is ametantrone, and the crystal has a crystal lattice in a P2$_1$ space group and unit cell dimensions of a=80.2±2 Å, b=176.8±3 Å, c 94.0±3 Å, and β=111.6±3 degree.

Other anticancer drugs can be readily introduced to form new drug-bound cleavage complexes by soaking the hTOPII$^{core}$-DNA crystals in a stabilization buffer containing the appropriate drug. Therefore, the present embodiments may be used to construct a high-throughput structural determination platform, by which the molecular bases of TOPII-targeting antineoplastic agents can be quickly examined.

Furthermore, the present disclosure also relates to a method for determining the crystal structure of the hTOPII$^{core}$-DNA-ligand ternary complex. For this purpose, crystals of hTOPII$^{core}$-DNA-ligand ternary complexes are first generated by performing the steps of the present methods described above. The thus obtained crystals are then subject to X-ray diffraction to generate X-ray diffraction data. The data are then recorded and optionally digitized. The three-dimensional structure of the crystal components may be solved by academically or commercially available softwares (such as HKL2000 program package from HKL Research).

As discussed hereinabove, the present crystal of an hTOPII$^{core}$-DNA binary complex could be used in a high throughput screening platform for identifying a ligand which is a hTOPII-targeting agent exhibiting inhibitory effect toward hTOPIIα and hTOPIIβ. As such, in another aspect, the present invention is directed to a high throughput screening platform for identifying a ligand which is a hTOPII-targeting agent exhibiting inhibitory effect toward hTOPIIα and hTOPIIβ.

According to one embodiment of the present invention, the high throughput screening platform comprises steps of: forming an hTOPII$^{core}$-DNA-ligand ternary complex by soaking a ligand into the crystal of hTOPII$^{core}$-DNA binary complex described above; obtaining an X-ray crystal diffraction pattern of the hTOPII$^{core}$-DNA-ligand ternary complex; and using the X-ray crystal diffraction pattern to analyze the structure of hTOPII$^{core}$-DNA ternary complex, and identify ligand-interacting residues on hTOPII.

In one example, hTOPII is hTOPIIα, and the first DNA strand has a sequence from 5' to 3',5'-NNNC-CGAGCNNNNGCTCGGNNN-3' (SEQ ID NO: 1), GCCGAGCTGCAGCTCGGC (SEQ ID NO: 2), or AGC-CGAGCTGCAGCTCGGCT (SEQ ID NO: 3). In another one example, hTOPII is hTOPIIβ, and the first DNA strand has the same sequence described above.

Moreover, the present disclosure also relates to an effective hTOPII-targeting agent for enhancing stability and specificity toward a DNA cleavage site comprising: a core domain of polycyclic ring system inserted into a DNA cleavage site, wherein the polycyclic ring system has a number of cyclic rings are 2, 3, or 4, and the individual ring is aromatic or non-aromatic.

In one example, the effective hTOPII-targeting agent further comprises at least one of a first branching moiety for fitting between a hTOP IIα and a DNA minor groove binding pocket, and the DNA minor groove binding pocket comprises amino acids residues including Pro439, Gly462, Asp463, Leu486, Arg487, Gly488, Asn504, Ala505, Glu506; some amino acid residues can make direct interactions with the aforementioned ones and the minor groove faces of nucleotides locating at or flanking the DNA cleavage site (including +1/+4; −1/+5; +2/+3 base pairs). Furthermore, the effective hTOPII-targeting agent further comprises at least one of a second branching moiety for protruding toward DNA major groove and fitting between hTOPIIα and a DNA major groove binding pocket, and the DNA major groove binding pocket comprises amino acids Met762 and Met766; the major groove faces of nucleotides locating at or flanking the DNA cleavage site (including +1/+4; −1/+5; +2/+3 base pairs). More specific targeting of hTOPIIα may be achieved by optimizing the shape and polarity complementation with the DNA major groove binding pocket of hTOPIIα.

In another example, the effective hTOPII-targeting agent further comprises at least one of a first branching moiety for fitting between a hTOPIIβ and a DNA minor groove binding pocket, and the DNA minor groove binding pocket comprises amino acids residues Pro455, Gly478, Asp479, Leu502, Arg503, Gly504, Asn520, Ala521, Glu522; some amino acid residues can make direct interactions with the aforementioned ones and the minor groove faces of nucleotides locating at or flanking the DNA cleavage site (including +1/+4; −1/+5; +2/+3 base pairs). Furthermore, the effective hTOPII-targeting agent further comprises at least one of a second branching moiety for protruding toward DNA major groove and fitting between is hTOPIIβ and a DNA major groove binding pocket, and the DNA major groove binding pocket comprises amino acids Gln778 and Met782, and the major groove faces of nucleotides locating at or flanking the DNA cleavage site (including +1/+4; −1/+5; +2/+3 base pairs). More specific targeting of hTOPIIβ may be achieved by optimizing the shape and polarity complementation with the DNA major groove binding pocket of hTOPIIβ.

In addition, the present invention also relates to a method for structural determination of the binary or ternary complex described herein. The method comprises steps of: (a) generating a crystal of the binary or ternary complex by performing the steps of the methods of the present invention; (b) generating and recording X-ray diffraction data of the crystal; (c) optionally, digitizing the data; (d) computationally reconstructing the data by X-ray diffraction; (e) determining the three-dimensional structure of the crystal components; and (f) storing the crystal coordinates generated on a data bank.

In a preferred embodiment of the present invention, the method for structure determination comprises additional steps of computer modeling, wherein computer modeling includes any one of the steps of (a) virtual-screening tools for the search of compounds that bind to the binding site of the hTOPII$^{core}$-DNA binary complex and make molecular contacts to the hTOPII portion and/or and the synthetic DNA; (b) using homology-modeling tools that search for compounds similar to known hTOPII-targeting agents (such as those described hereinabove) and that make molecular contacts to the hTOPII portion and/or and the synthetic DNA; (c) using molecular-modeling algorithms that allow an estimation of the binding affinities of compounds to the hTOPII$^{core}$-DNA binary complex; or (d) using ligand construction tools that build up organic molecules that fit into the ligand binding site of the hTOPII$^{core}$-DNA binary complex.

The design of molecules with particular structural relationships to part of a protein molecule is well known to those with ordinary skills in the art. Any of these so-called "molecular modeling" methods for rational drug design can be used to find a ligand to the hTOPII$^{core}$-DNA binary complex that behaves analogously or similar to any one of the etoposide, mitoxantrone, doxorubicin or amsacrine. Most of these molecular modeling methods take into consideration the shape, charge distribution and the distribution of hydrophobic groups, ionic groups and hydrogen bonds in the site of interest of the hTOPII$^{core}$-DNA binary complex. Using this information, that can be derived from the crystal structures of hTOPII$^{core}$-DNA binary complex and hTOPII$^{core}$-DNA-ligand ternary complex, these methods either suggest improvements to existing proposed molecules, construct new molecules on their own that are expected to have good binding affinity, screen through virtual compound libraries for such molecules, or otherwise support the interactive design of new drug compounds in silico. Any conventional virtual screening programs designed to calculate the binding position and conformation as well as the corresponding binding energy of a compound to a protein-DNA binary complex could be used for this purpose.

The following Examples are provided to elucidate certain aspects of the present invention and to aid those of skilled in the art in practicing this invention. These Examples are in no way to be considered to limit the scope of the invention in any manner.

EXAMPLES

The synthetic double-stranded DNA, hTOPIIα and hTOPIIβ portion for producing crystals of hTOPIIα$^{core}$-DNA binary complexes (examples 1-5), hTOPIIβ$^{core}$-DNA binary complexes (examples 6-10) and uses thereof of the present disclosure will be described in further detail with reference to several examples below, which are not intended to limit the scope of the present disclosure.

Example 1

Construction and Expression of hTOPIIα$^{core}$ Construct

The coding sequence of hTOPIIα$^{core}$ (residues 429-4187) was amplified by PCR using the YEphTOPIIα plasmid (containing the full-length human TOPIIα gene) as a template and the following oligonucleotide primers: forward primer (SEQ ID NO: 4, 5'-ACGC GTCGACATGTCTGTTGAAAGAATCTATCA-3'), and a reverse primer (SEQ ID NO: 5, 5'-GCAGTC GAGCTCCATCTTGTTTTTCCTTGGCTT-3') obtained from =GENE Co. (Taipei. Taiwan). The restriction sites of Sal I and Sac I are underlined. The resulting cDNA was cloned into the plasmid pET51b (name of the provider) for expression of the recombinant protein with the Strep II tag at the N-terminus and the hexa-His tag at the C-terminus. This plasmid (named 51bDBCCα) was co-transformed with the pLysS plasmid into *Escherichia coli* BL21 (DE3) Star. For expression, after bacterial growth in Luria Broth (LB) medium at 37° C. to $OD_{600}$=0.8, isopropylthiogalactoside (IPTG) was added to a final concentration of 0.3 mM, and protein expression was induced at 16° C. for 16 h. Bacteria were harvested by centrifugation and stored at −80° C. until further use.

Example 2

Protein Purification

The *E. coli* cell pellet was resuspended in lysis buffer (50 mM sodium phosphate (NaPi) pH 7.4, 10% glycerol, 500 mM NaCl, 5 mM β-mercaptoethanol, 0.5 mM phenylmethanesulfonyl fluoride, and 10 mM imidazole), and the cells were disrupted by sonication. The crude cell extract was centrifuged at 27,216×g for 120 min at 4° C. and loaded onto a nickel-nitrilotriacetic acid (Ni-NTA) column. The column was washed to baseline, and the protein was eluted with elution buffer (lysis buffer containing 250 mM imidazole). The resulting protein sample was dialyzed against buffer A (30 mM Tris-HCl, pH 7.5, 15 mM NaCl, 2 mM β-mercaptoethanol, and 1 mM EDTA) at 4° C. for 4 h and loaded onto a HiPrep 16/10 Heparin Fast Flow column. The protein was eluted in a linear gradient over 10 column volumes with buffer B (buffer A containing 1 M NaCl). The eluted fractions were pooled and purified on a size-exclusion column (Hi-Load Superdex 200) in gel filtration buffer (50 mM Tris-HCl, pH 7.0, 200 mM KCl, 5 mM $MnCl_2$, 2 mM β-mercaptoethanol, and 1 mM EDTA). The dimer-form protein (around 180 kDa) was collected and concentrated to 10 mg/ml for crystallization.

Example 3

Synthetic Double-Stranded DNA for Crystallography

The design of the oligonucleotide sequence 5'-AGC-CGAGCTGCAGCTCGGCT-3'(SEQ ID NO:3) of the double-stranded DNA substrate was based on the cleavage pattern of human TOPII treated with anticancer drugs including etoposide (VP-16), teniposide (VM-26) and mitoxantrone. The oligonucleotide was synthesized by VIOGENE Co. (Taipei, Taiwan) on order. The oligonucleotides were dissolved in buffer containing 30 mM Tris-HCl, 70 mM NaCl, 2 mM 3-mercaptoethanol, and 1 mM EDTA and annealed at 55° C. to generate double-stranded DNA for crystallization.

Example 4

Crystallization

The protein sample was mixed with final concentration 2 mM mitoxantrone and DNA substrate (in a 1.2-fold molar ratio to protein). Initial crystallization trials for the hTOPIIα$^{core}$-DNA-mitoxantrone ternary complex were performed with commercially available kits (Hampton Research) using the hanging drop vapor diffusion method. Specifically, 1 μl of concentrated hTOPIIα$^{core}$-DNA-mitoxantrone solution in gel filtration buffer was mixed with an equal amount of reservoir solution and equilibrated against 200 μl of reservoir solution at 4° C. Conditions that produced small crystals were refined by systematic variation of the precipitant concentration and pH. The hTOPIIα$^{core}$-DNA-mitoxantrone ternary complex was crystallized by the hanging-drop vapor diffusion method using 100 mM magnesium acetate, 50 mM 2-(N-morpholino)ethanesulfonic acid pH 5.6, and 25% 2-methyl-2,4-pentanediol (MPD) as the precipitating agent. Single crystals suitable for data collection can be obtained after several months.

Example 5

Structure Determination

The diffraction data on the hTOPIIα$^{core}$-DNA-mitoxantrone complex were collected at NSRRC, Taiwan (beamline BL13C1). The diffraction data were is processed using the HKL2000 program suite (Otwinowski, Z. & Minor, W. Processing of X-Ray Diffraction Data Collected in Oscillation Mode. Methods Enzymol 267, 307 (1997)). The structure of hTOPIIα$^{core}$-DNA-mitoxantrone was solved by molecular replacement with the AutoMR and AutoBuild modules in the Phenix program suite (Zwart, P. H. et al. Automated structure solution with the PHENIX suite. Methods Mol Biol 426, 419-435 (2008)) using the hTOPIIβ$^{core}$-DNA-etoposide structure of *H. sapiens* TOPII (Protein Data Bank code 3QX3) as the search model. The resulting electron density map was of excellent quality and showed clearly the densities of the bound DNA and mitoxantrone, the structures of DNA and drug were built into the density using Coot (Ernsley, P. & Cowtan, K. Coot: model-building tools for molecular graphics. Acta Crystallogr D Biol Crystallogr 60, 2126-2132 (2004)). Detailed refinement parameters of the structure are listed in Table 1

TABLE 1

| Summary of crystallographic analysis | |
|---|---|
| Structure | hTOPIIα-DNA-mitoxantrone ternary complex |
| Space group | $P2_122_1$ |
| Unit cell dimensions | |
| a, b, c (Å) | 105.4, 126.2, 198.0 |
| Data collection | |
| Wavelength (Å) | 0.97622 |
| Resolution (Å) | 30.0-2.58 |
| last shell | 2.62-2.58 |

TABLE 1-continued

Summary of crystallographic analysis

| Structure | hTOPIIα-DNA-mitoxantrone ternary complex |
|---|---|
| Observed reflections | 337381 |
| Unique reflections | 79130 |
| Completeness (%) | 94.5 |
| last shell | 96.4 |
| Multiplicity | 4.4 |
| Mean $I/\sigma$ (last shell) | 11.5 (2.2) |
| $R_{sym}{}^{a}$ (last shell) (%) | 0.078 (0.488) |
| Refinement | |
| Resolution range (Å) | 28.3-2.58 |
| No. of reflection in working set (test set) | 79084 (3943) |
| $R_{cryst}{}^{b}$ (%) | 0.205 |
| $R_{free}{}^{b}$ (%) | 0.232 |

$R_{sym} = (\Sigma|Ihkl - \langle \rangle|)/(\Sigma Ihkl)$, where the average intensity $\langle \rangle$ is taken overall symmetry equivalent measurements, and Ihkl is the measured intensity for any given reflection.
$^{b}R_{cryst} = (\Sigma||F_o| - k|F_c||)/(\Sigma|F_o|)$. $R_{free} = R_{cryst}$ for a randomly selected subset (5%) of the data that were not used for minimization of the crystallographic residual.

Example 6

Construction and Expression of hTOPII$^{core}$ Construct

The coding sequence of the protomer (i.e., the DNA-binding and cleavage core) of hTOPIIβ$^{core}$ (residues 445-1201) was amplified by polymerase chain reaction (PCR) using the YEphTOPIIβ plasmid, which contains the full-length human TOPIIβ gene (it was kindly provided by Dr. Leroy F. Liu, Dept. of Pharmacology, UMDNJ-Robert Wood Johnson, Medical School, of New Jersey, U.S.A.) as a template with a forward primer (SEQ ID NO: 6, 5'-ACGC GTCGACTCAGTAAAATACAGTAAAATCAAAGGTAT-TCC-3') and a reverse primer (SEQ ID NO: 7, 5'-GCAGTC GAGCTCCATCTTCTCGTTCTTGAGATTCCACTTT-3') obtained from VIOGENE Co. (Taipei, Taiwan). The restriction sites of Sal I and Sac I are respectively underlined. The resulting cDNA was cloned into the plasmid pET51b (name of the provider) for expression of the recombinant protein with the Strep II tag at the N-terminus and the hexa-His tag at the C-terminus. This plasmid (named 51bDBCCβ) was co-transformed with the pLysS plasmid into *Escherichia coli* BL21 (DE3) Star. For expression, after bacterial growth in Luria Broth (LB) medium at 37° C. to OD$_{600}$=1.0, isopropylthiogalactoside (IPTG) was added to a final concentration of 0.3 mM, and protein expression was induced at 20° C. for 16 h. Bacteria were harvested by centrifugation and stored at −80° C. until further use.

Example 7

Protein Purification

The *E. coli* cell pellet was re-suspended in lysis buffer (50 mM sodium phosphate (NaPi) pH 7.4, 10% glycerol, 500 mM NaCl, 5 mM β-mercaptoethanol, 0.5 mM phenylmethanesulfonyl fluoride, and 10 mM imidazole), and the cells were disrupted by sonication. The crude cell extract was centrifuged at 27,216×g for 120 min at 4° C. and loaded onto a nickel-nitrilotriacetic acid (Ni-NTA) column. The column was washed to baseline, and the protein was eluted with elution buffer. (the lysis buffer except containing 250 mM imidazole). The resulting protein sample was dialyzed against buffer A (30 mM Tris-HCl, pH 7.5, 15 mM NaCl, 2 mM β-mercaptoethanol, and 1 mM EDTA) at 4° C. for 4 h and loaded onto a HiPrep 16/10 Heparin Fast Flow column. The protein was eluted in a linear gradient over 10 column volumes with buffer B (buffer A except containing 1 M NaCl). The eluted fractions were pooled and purified on a size-exclusion column (Hi-Load Superdex 200) in gel filtration buffer (buffer A except containing 70 mM NaCl). The dimer-form protein (around 180 kDa) was collected and concentrated to 6.5 mg/ml for crystallization.

Example 8

Synthetic Double-Stranded DNA for Crystallography

The design of the oligonucleotide sequence 5'-AGC-CGAGCTGCAGCTCGGCT-3' (SEQ ID NO: 3) of the double-stranded DNA substrate was based on the cleavage pattern of human TOPII treated with anticancer drugs, including etoposide (VP-16), teniposide (VM-26) and mitoxantrone. The oligonucleotide was synthesized by VIOGENE Co. (Taipei, Taiwan) on order. The oligonucleotides were dissolved in a buffer containing 30 mM Tris-HCl, 70 mM NaCl, 2 mM β-mercaptoethanol, and 1 mM EDTA and annealed at 55° C. to generate double-stranded DNA for crystallization.

Example 9

Crystallization

Crystals were grown at 4° C. by hanging drop vapor diffusion. The protein sample in gel filtration buffer of Example 2 was first mixed with 2 mM etoposide (in DMSO), and then mixed with the double-stranded DNA of Example 3 in a molar ratio of DNA to protein equals 1.2 to form the hTOPIIβ-DNA-etoposide solution. A reservoir solution comprising 100 mM magnesium acetate, 50 mM 2-(N-morpholino) ethanesulfonic acid (pH 5.8), and 22% 2-methyl-1,6-hexanediol (MPD) was also prepared. The crystallization drop was obtained by mixing 1 µl of the hTOPIIβ-DNA-etoposide solution with an equal amount of reservoir solution. Then the crystallization drop (2 µl) was equilibrated against 200 µl of reservoir solution at 4° C. Single crystals suitable for data collection appeared within a week, and the crystals were removed from the crystallization drop. To obtain crystals of hTOPIIβ-DNA binary complexes, the crystals of the hTOPIIβ-DNA-etoposide ternary complexes were placed in a fresh reservoir solution comprising 30% MPD for 16 hours to soak out the bound etoposide.

Afterwards, doxorubicin, mitoxantrone, ametantrone and amsacrine were respectively soaked in by adding 1 mM drug (in DMSO) to the respective crystallization drop containing crystals of hTOPIIβ$^{core}$-DNA binary complexes for 16 hours to obtain hTOPIIβ$^{core}$-DNA-mitoxantrone ternary complexes, hTOPIIβ$^{core}$-DNA-doxorubicin ternary complexes, hTOPIIβ$^{core}$-DNA-ametantrone ternary complexes and hTOPIIβ$^{core}$-DNA-amsacrine ternary complexes respectively. All crystals were harvested by transferring into a fresh reservoir solution comprising 30% MPD before looping and flash-freezing in liquid nitrogen for data collection.

Example 10

Structure Determination

The diffraction data on the crystals of hTOPIIβ$^{core}$-DNA-etoposide complexes were collected at Sring-8, Japan (beamline BL12B2). The diffraction data on the crystals of hTOPIIβ$^{core}$-DNA-mitoxantrone, hTOPIIβ$^{core}$-DNA-doxorubicin, hTOPIIβ$^{core}$-DNA-ametantrone, hTOPIIβ$^{core}$-DNA-amsacrine, and hTOPIIβ$^{core}$-DNA complexes of Example 4 were collected at National Synchrontron Radiation Research Center (NSRRC), Taiwan (beamlines BL13B1 and BL13C1). All diffraction data were processed using the HKL2000 program suite. The crystal structure of the hTOPIIβ$^{core}$-DNA-etoposide complex was solved by molecular replacement with the AutoMR and AutoBuild modules in the Phenix program suite using the DNA-free polyalanine structure of S. cerevisiae TOPII (Protein Data Bank code 3L4K) as the search model. The resulting electron density map was of excellent quality and showed clearly the densities of the bound DNA and etoposide, the structures of DNA and drug were built into the density using Coot. The crystal structures of the hTOPIIβ$^{core}$-DNA-mitoxantrone, hTOPIIβ$^{core}$-DNA-doxorubicin, hTOPIIβ$^{core}$-DNA-ametarttrone, hTOPIIβ$^{core}$-DNA-amsacrine, and hTOPIIβ$^{core}$-DNA complexes were solved by directly inputting the respective diffraction data sets into rigid body refinement using the (etoposide-deleted) hTOPIIβ$^{core}$-DNA-etoposide structure as the starting model. All structures then underwent rounds of manual model rebuilding and refinement with Coot and Phenix. One cleavage complex molecule was present in the asymmetric unit. Three-dimensional molecular structures in the present disclosure were generated with PyMol software package (Schrodinger, LIC).

Missing residues in each structure are as follows: hTOPIIβ$^{core}$-DNA-etoposide: 445-451, 592-637, 697-706, and 1112-1134 in chain A and 445-448, 593-636, 696-705, 963-966, and 1111-1134 in chain B; hTOPIIβ$^{core}$-DNA-mitoxantrone: 445-451, 592-645, 697-706, and 1112-1134 in chain A and 445-448, 591-636, 694-706, 963-966, and 1111-1134 in chain B; hTOPIIβ$^{core}$-DNA-doxorubicin: 445-454, 591-637, 697-706, and 1112-1134 in chain A and 445-448, 591-636, 696-705, 963-966, and 1111-1134 in chain B; hTOPIIβ$^{core}$-DNA-amsacrine: 445-454, 592-647, 694-706, and 1112-1134 in chain A and 445-452, 591-635, 694-705 and 1111-1134 in chain B; TOPIIβ$^{core}$-DNA-ametantrone: 445-451, 592-644, 697-706, and 1112-1134 in chain A and 445-448, 593-643, 696-705, 963-966, and 1111-1134 in chain B; hTOPIIβ$^{core}$-DNA: 445-454, 592-639, 697-706, and 1112-1134 in chain A and 445-448, 593-636, 696-705, 963-966, and 1111-1134 in chain B. These regions were omitted from the model. Although in all structures Asp1101 of both chains fell in the disallowed region of the Ramachandran plot, they fit very well to the corresponding electron density. Detailed refinement parameters of the four structures are listed in Table 2a and 2b.

TABLE 2a

Summary of crystallographic analysis

| Structure | hTOPIIβ-DNA-etoposide ternary complex | hTOPIIβ-DNA-mitoxantrone ternary complex | hTOPIIβ-DNA-doxorubicin ternary complex | hTOPIIβ-DNA binary complex |
|---|---|---|---|---|
| Space group | P2$_1$ | P2$_1$ | P2$_1$ | P2$_1$ |
| Unit cell dimensions | | | | |
| a, b, c (Å) | 80.2, 176.8, 94.0 | 80.5, 176.6, 93.8 | 80.3, 176.6, 94.0 | 80.0, 176.4, 94.2 |
| β (degrees) | 111.6 | 111.5 | 111.5 | 112.1 |
| Data collection | | | | |
| Wavelength (Å) | 0.90000 | 0.97622 | 0.97622 | 0.97622 |
| Resolution (Å) | 30.0-2.16 | 30.0-2.55 | 30.0-2.68 | 30.0-2.30 |
| last shell | 2.20-2.16 | 2.59-2.55 | 2.73-2.68 | 2.34-2.30 |
| Observed reflections | 327364 | 283116 | 529470 | 318732 |
| Unique reflections | 123847 | 78830 | 68785 | 103829 |
| Completeness (%) | 95.7 | 99.4 | 100.0 | 94.4 |
| last shell | 98.2 | 97.3 | 100.0 | 99.0 |
| Multiplicity | 2.6 | 3.6 | 7.7 | 3.1 |
| Mean $I/\sigma$ (last shell) | 16.9 (2.1) | 12.1 (2.5) | 12.4 (4.9) | 13.4 (2.6) |
| $R_{sym}{}^a$ (last shell) (%) | 0.06 (0.47) | 0.07 (0.49) | 0.09 (0.47) | 0.06 (0.49) |
| Refinement | | | | |
| Resolution range (Å) | 29.55-2.16 | 29.94-2.55 | 28.64-2.68 | 27.31-2.30 |
| NO: of reflection in working set (test set) | 117720 (5917) | 75507 (3790) | 67109 (3383) | 99340 (4954) |
| $R_{cryst}{}^b$ (last shell) (%) | 0.17 | 0.16 | 0.16 | 0.18 |
| $R_{free}{}^b$ (last shell) (%) | 0.21 | 0.21 | 0.21 | 0.22 |
| r.m.s. deviation from ideal | | | | |
| Bond lengths (Å) | 0.007 | 0.008 | 0.007 | 0.007 |
| Bond angles (degrees) | 1.042 | 1.102 | 1.118 | 1.082 |
| Ramachandran | | | | |
| Outliers (%) | 0.1 | 0.2 | 0.2 | 0.2 |
| Favored (%) | 97.1 | 96.1 | 96.0 | 97.0 |

$^a R_{sym} = (\Sigma|Ihkl - \langle I \rangle|)/(\Sigma Ihkl)$, where the average intensity $\langle I \rangle$ is taken overall symmetry equivalent measurements, and Ihkl is the measured intensity for any given reflection.
$^b R_{cryst} = (\Sigma||F_o| - k|F_c||)/(\Sigma|F_o|)$. $R_{free} = R_{cryst}$ for a randomly selected subset (5%) of the data that were not used for minimization of the crystallographic residual.

TABLE 2b

Summary of crystallographic analysis

| Structure | hTOPIIβ$^{core}$-DNA-amsacrine ternary complex | hTOPIIβ$^{core}$-DNA-ametantrone ternary complex |
|---|---|---|
| Space group | P2$_1$ | |
| Unit cell dimensions | | |
| a, b, c (Å) | 80.2, 176.8, 94.0 | |
| β (degrees) | 111.6 | |
| Data collection | | |
| Wavelength (Å) | 0.97622 | 1.00000 |
| Resolution (Å) (last shell$^a$) | 30.0-2.70 (2.75-2.70) | 30.0-2.70 (2.75-2.70) |
| Observed reflections | 188131 | 242273 |
| Unique reflections | 63644 | 65943 |
| Completeness (%) (lastshell$^a$) | 97.4 (98.8) | 99.1 (91.7) |
| Multiplicity | 3.0 | 3.7 |
| Mean⟨ I/σ⟩ (last shell$^a$) | 10.4 (2.6) | 12.4 (2.5) |
| R$_{sym}$$^b$ (%) (last shell$^a$) | 0.08 (0.47) | 0.09 (0.42) |
| Refinement | | |
| Resolution range (Å) | 28.23-2.70 | 27.50-2.70 |
| No. of reflection in working set (test set) | 63605 (3235) | 65898 (3340) |
| R$_{cryst}$$^c$ (%) | 0.16 | 0.17 |
| R$_{free}$$^c$ (%) | 0.22 | 0.22 |
| r.m.s. deviation from ideal | | |
| Bond lengths (Å) | 0.008 | 0.008 |
| Bond angles (degrees) | 1.180 | 1.158 |
| Ramachandran analysis$^d$ | | |
| Outliers (%) | 0.2 | 0.2 |
| Favored (%) | 96.4 | 96.6 |

$^a$Statistics for data from the highest resolution shell of 2.75-2.70 Å (amsacrine-ternary complex) and 2.75-2.70 Å (ametantrone-ternary complex).
$^b$R$_{sym}$=(Σ|Ihkl −⟨ ⟩ )/(ΣIhkl), where the average intensity⟨ ⟩ is taken overall symmetry equivalent measurements, and Ihkl is the measured intensity for any given reflection.
$^c$R$_{cryst}$=(Σ||F$_o$| − k|F$_c$||)/(Σ|F$_o$|). R$_{free}$=R$_{cryst}$ for a randomly selected subset (5%) of the data that were not used for minimization of the crystallographic residual.
$^d$Categories were defined by PHENIX. All non-glycine residues are included for this anlaysis.

Figure 1F:
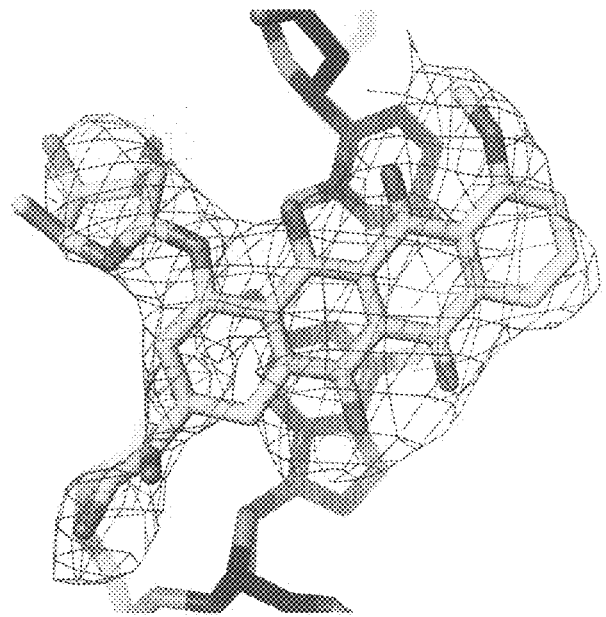
Figure 1E:
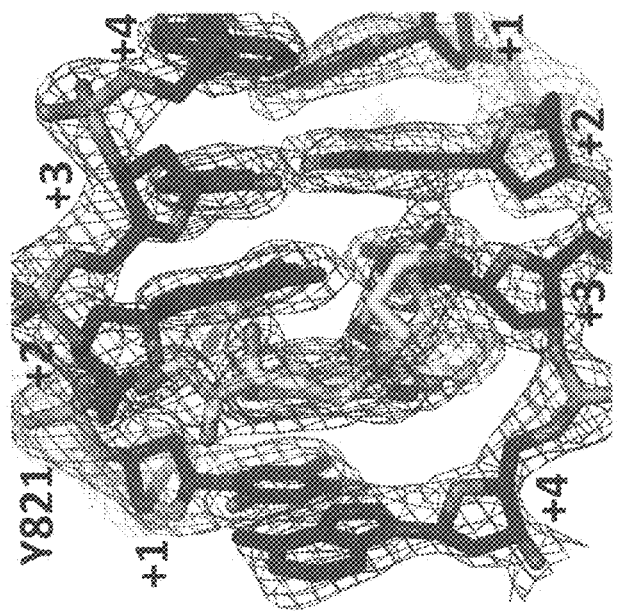

FIGS. 1A to 1E are Electron density maps of the drug-binding sites and the bound anticancer drugs. The final 2F$_o$-F$_c$ maps (left panel; contoured at 1.2σ) depict the electron densities around the binding sites of etoposide (FIGS. 1A and 1B), mitoxantrone (FIGS. 1C and 1D), and doxorubicin (FIGS. 1E and 1F). The unbiased F$_o$-F$_c$ electron density maps (contoured at 2.8a) for the bound anticancer drugs are illustrated in the right panel. All DNA base pairs and the presence of two ligand molecules and six Mg$^{2+}$ ions per complex are clearly visible in the electron density maps. The observation of phosphotyrosyl linkages between the two active site tyrosine residues (Tyr821) and the scissile phosphates, accompanied by the rupture of phosphodiester bonds, confirms the formation of the cleavage complex.

Figure 2A:
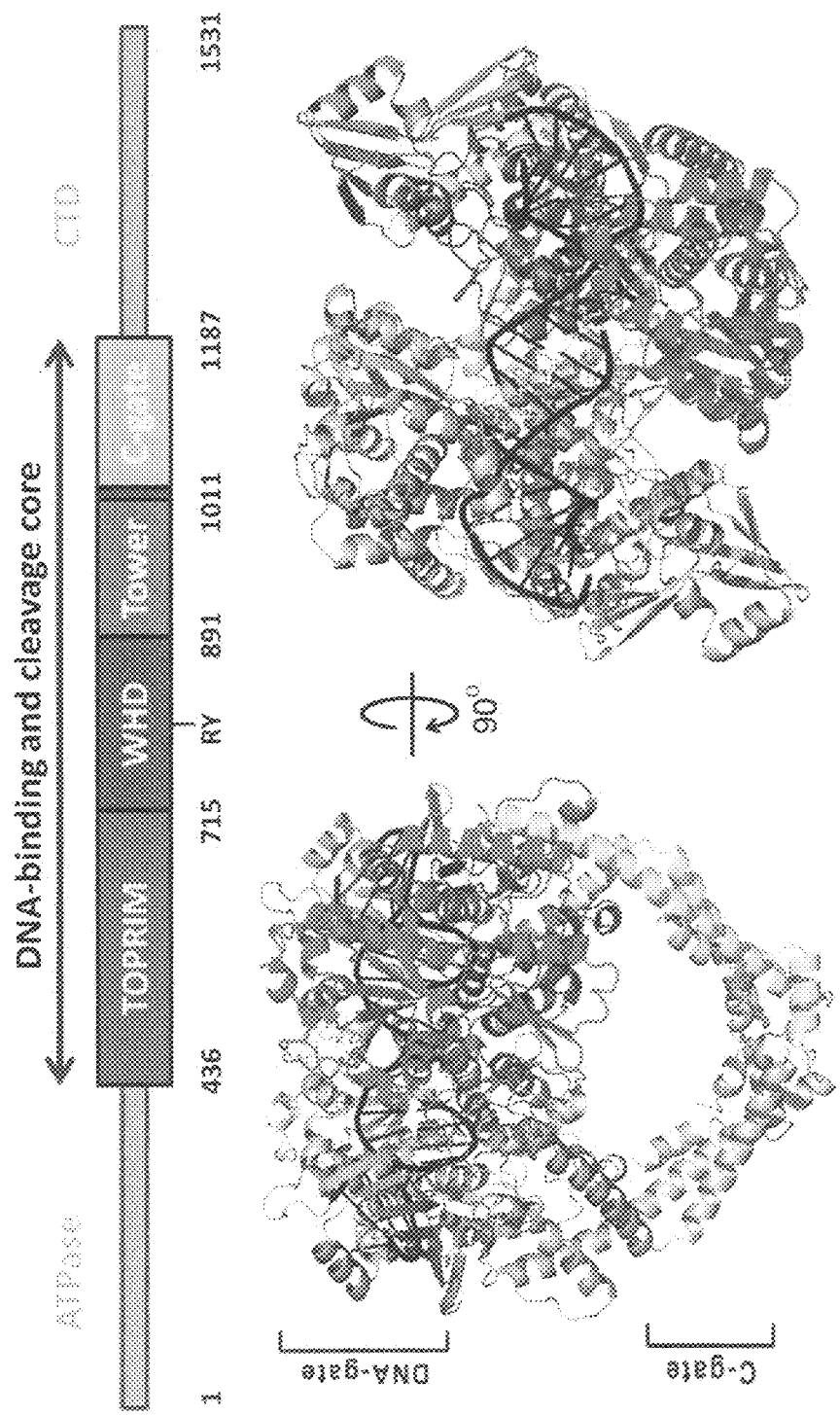
FIG. 2A depicts linear domain organization and overall structure of the hTOPIIα$^{core}$-DNA-mitoxantrone ternary complex.
Figure 2B:
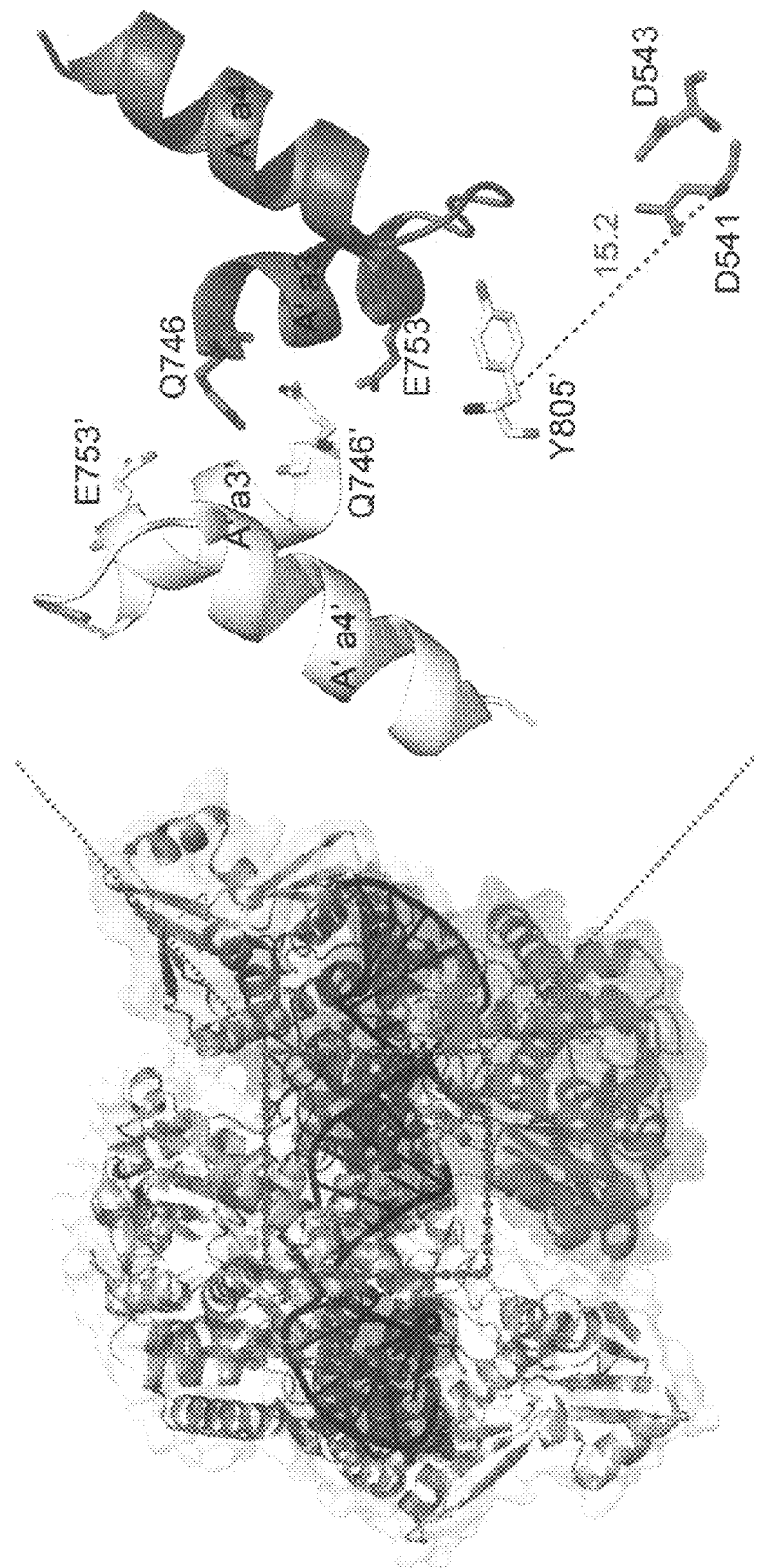
FIG. 2B illustrates the surface representation of hTOPII-α$^{core}$-DNA-mitoxantrone ternary complex (left; oriented and colored as in FIG. 2A). Note the presence of holes along the dimer interface, which indicates a looser packing between the two monomers, and the selected residues from the enclosed region are shown in an enlarged view (right) to illustrate the spatial relation between the catalytic tyrosine (Tyr805) and the metal-binding residues (Asp541 and Asp543)
Figure 2C:
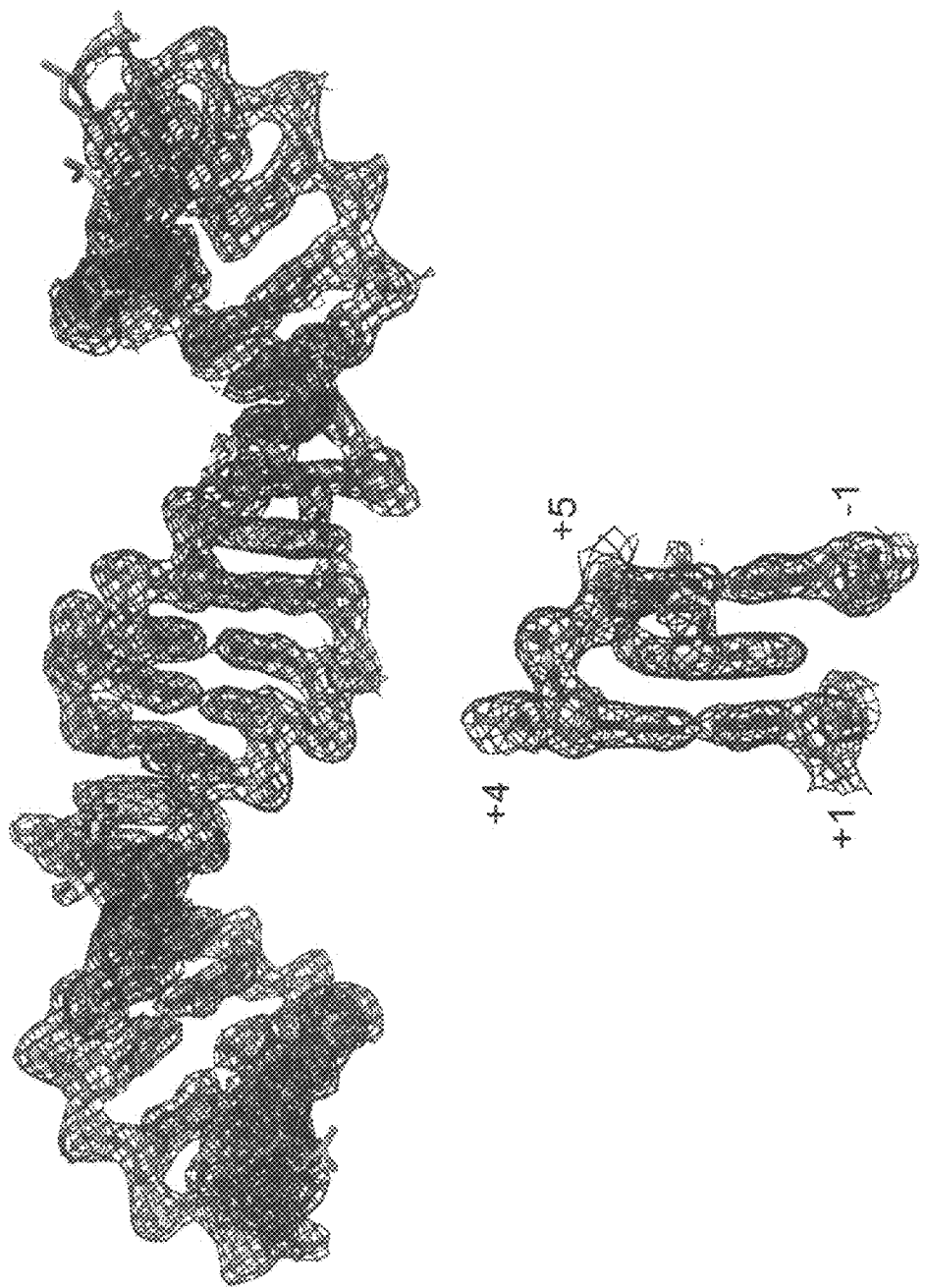
FIG. 2C illustrates the electron density maps of the bound DNA and mitoxantrone in the hTOPIIα$^{core}$-DNA-mitoxantrone ternary complex.
Figure 2D:
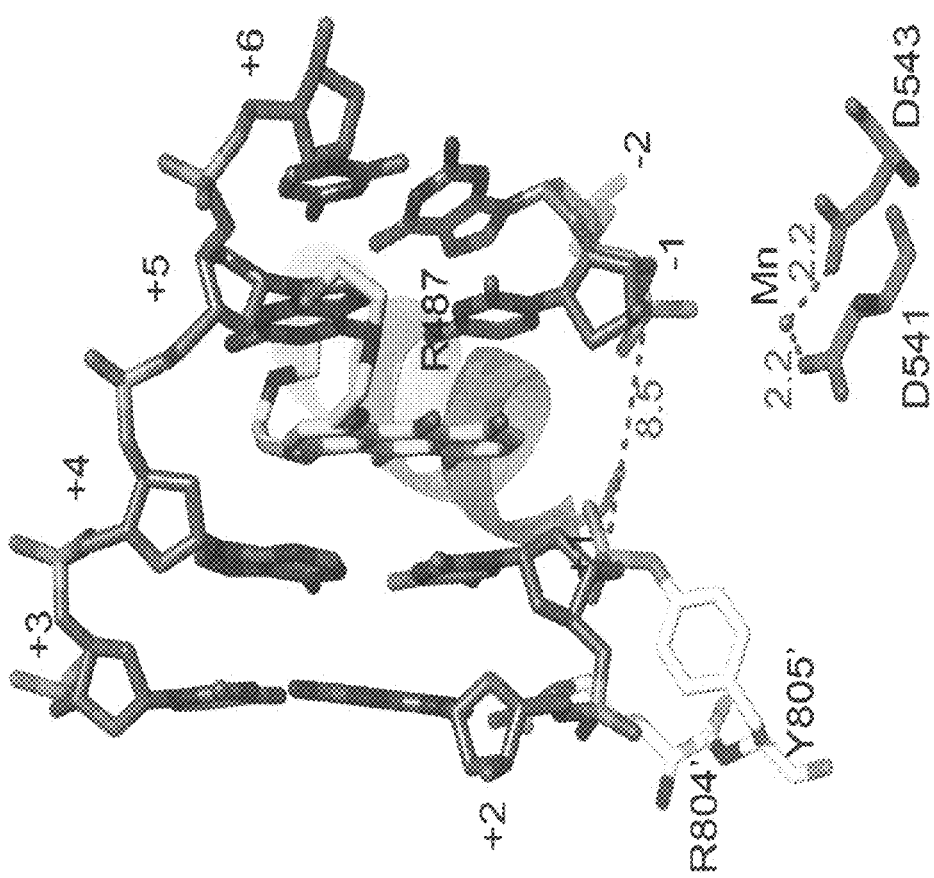
FIGS. 2D-2E illustrate close-up view of the mitoxantrone-stabilized cleavage site viewing form DNA minor groove and major groove, respectively.
Figure 2E:
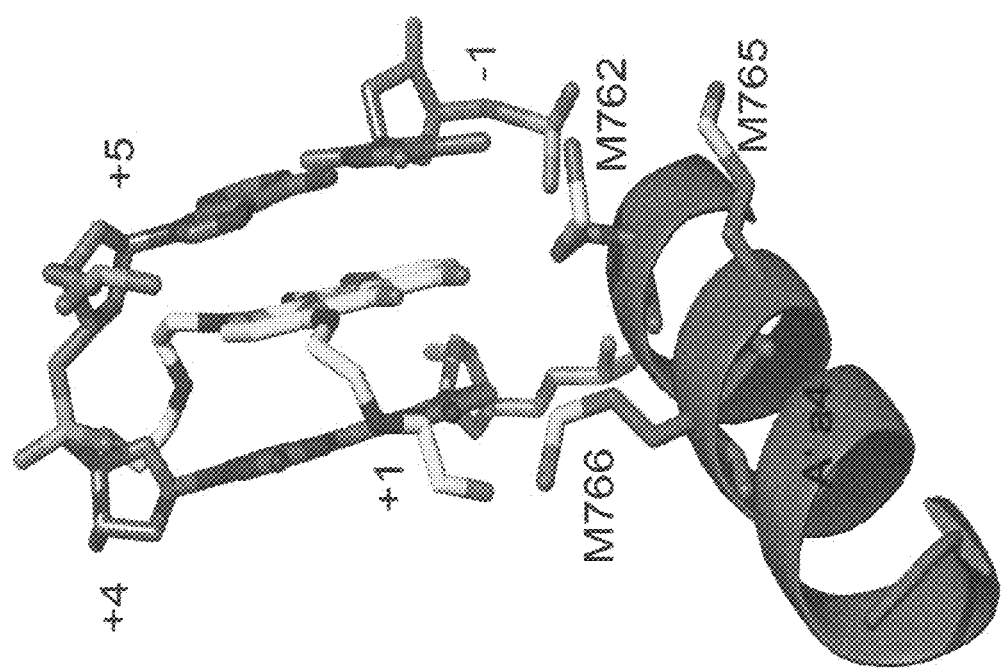
Figure 2F:
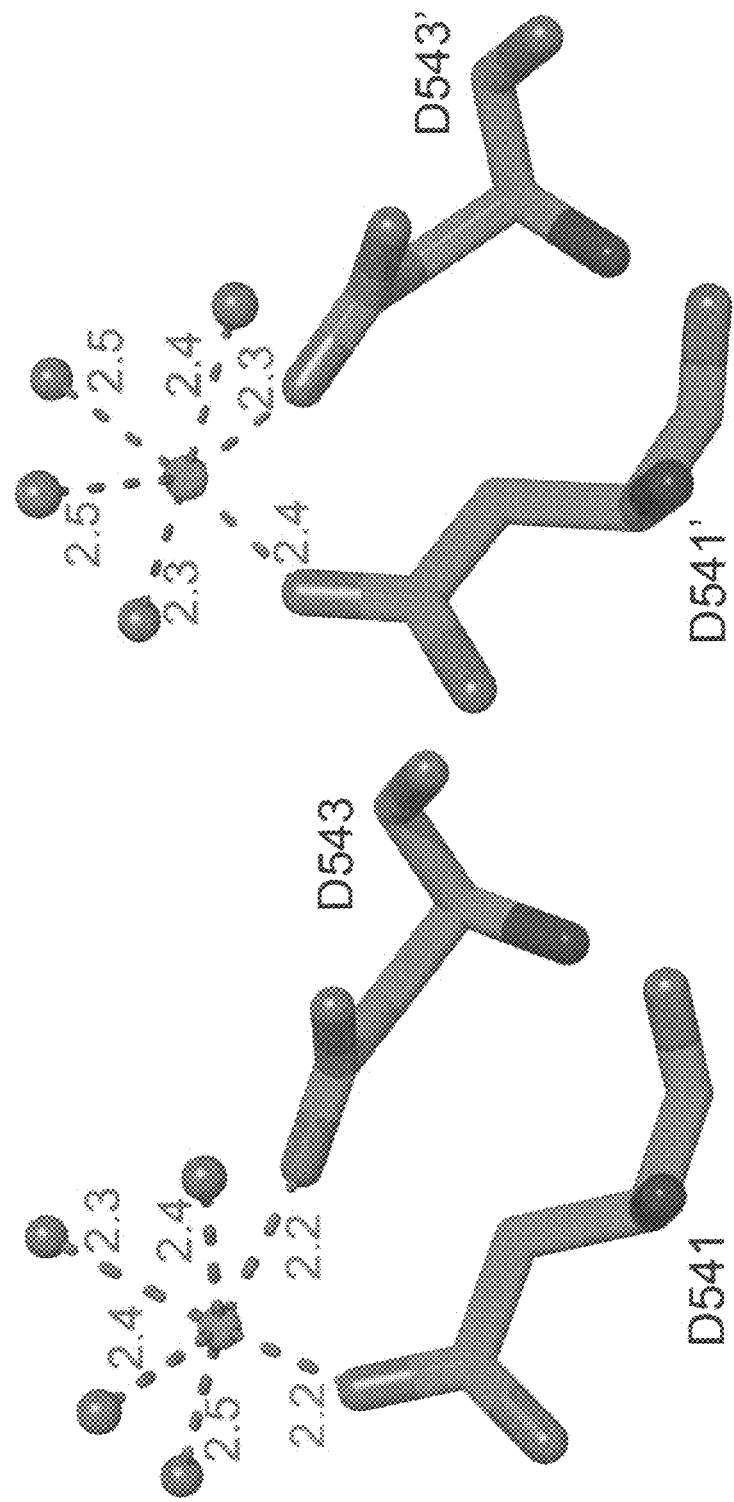
FIG. 2F illustrates the coordination of metals observed in the hTOPIIα$^{core}$-DNA-mitoxantrone ternary complex.

FIG. 2A depicts the structure of the hTOPIIα$^{core}$-DNA-mitoxantrone ternary complex. The middle fragment (residues 436 to 1187), corresponding to hTOPIIα$^{core}$, was used in the present invention. Orthogonal views of the ternary cleavage complex. DNA is in blue, one hTOPIIα$^{core}$ monomer is in gray, and the other follows the scheme shown in linear picture. FIG. 2B illustrates the surface representation of hTOPIIα$^{core}$ (oriented and colored as in FIG. 2A) as observed in the mitoxantrone-stabilized ternary cleavage complex (left). Note the presence of holes along the dimer interface, which indicates a looser packing between the two monomers, and the selected residues from the enclosed region are shown in an enlarged view (right) to illustrate the spatial relation between the catalytic tyrosine and the metal-binding residues; the distance between catalytic tyrosine and one aspartate (D541 of hTOPIIα) of the metal-binding residues is indicated. Residues from different monomers are colored differently, with labels belonging to the second monomer flagged by a prime. FIG. 2C illustrates the electron density maps of the bound DNA and mitoxantrone in the hTOPIIα$^{core}$-DNA-mitoxantrone ternary cleavage complex. The final 2F$_o$-F$_c$ maps (upper panel, contoured at 1.5σ) showing clear electron density for all 20 DNA base pairs. The final 2 F$_o$-F$_c$ map (bottom panel, contoured at 1.5σ) for the bound mitoxantrone. Close-up view of the mitoxantrone-stabilized cleavage site is illustrated in FIG. 2D. DNA is shown in blue, and the two hTOPII-α$^{core}$ monomers are colored differently. Labels belonging to the second monomer are flagged by a prime. The Mn$^{2+}$ that occupies the Mg$^{2+}$ binding site is shown. The distance between the Y805'-linked scissile phosphate and the 3'-OH is around 6.5 Å. Referring to FIG. 2E, interactions observed in the mitoxantrone binding site suggest that the structure-activity relationships of mitoxantrone derivatives. FIG. 2F illustrates the coordination of metals observed in the hTOPII-α$^{core}$-DNA-mitoxantrone ternary cleavage complex. Each of the Mn$^{2+}$-chelating residues (two aspartates) of the TOPRIM domain donates a side chain oxygen for metal coordination. Labels belonging to the second monomer are flagged by a prime. Mn$^{2+}$ and water are shown as green and red spheres, respectively.

Figure 3A:
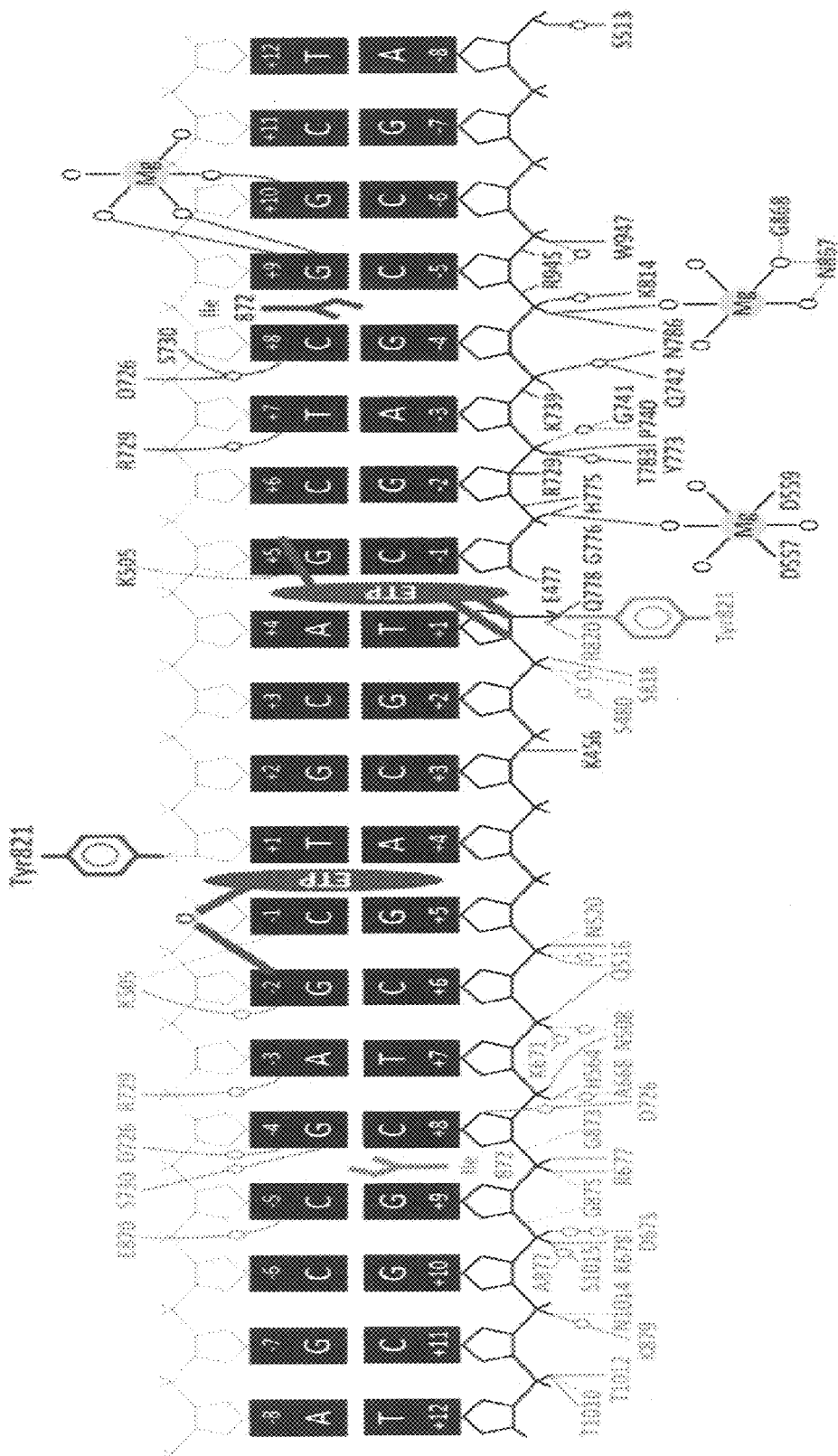
FIGS. 3A to 3D illustrate the protein-DNA interactions observed in the hTOPIIβ$^{core}$-DNA-etoposide ternary complex, hTOPIIβ$^{core}$-DNA-mitoxanterone ternary complex, hTOPIIβ$^{core}$-DNA-doxorubicin ternary complex, and drug-free hTOPIIβ$^{core}$-DNA binary complex, respectively.
Figure 3D:
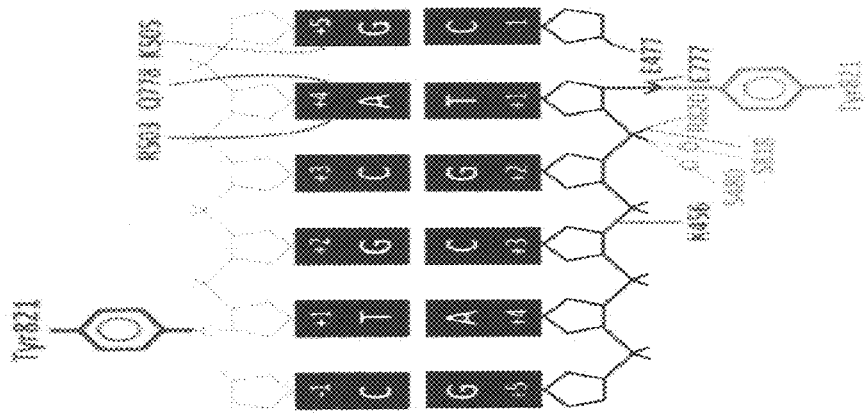
Figure 3C:
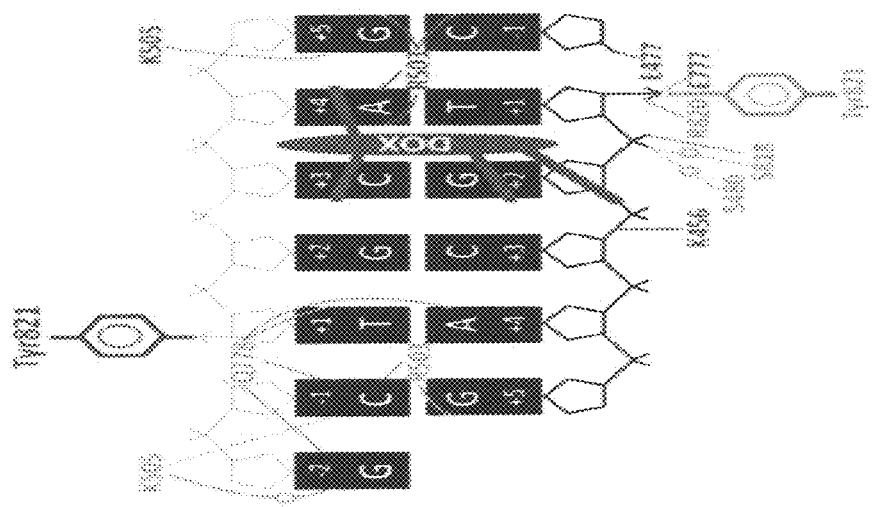
Figure 3B:
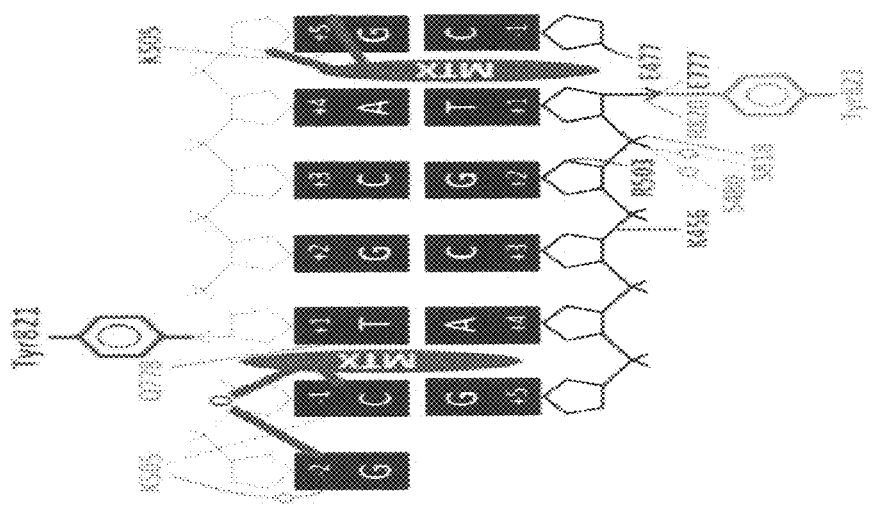

This high resolution structure reveals the detailed interplay between the protein, the DNA, and the drugs. FIGS. 3A to 3D illustrate the protein-DNA interactions observed in the hTOPIIβ$^{core}$-DNA-etoposide ternary complex, hTOPIIβ$^{core}$-DNA-mitoxanterone ternary complex, hTOPIIβ$^{core}$-DNA-doxorubicin ternary complex, and drug-free hTOPIIβ$^{core}$-DNA binary complex, respectively. Residues from different protomers are colored differently (green and blue). The bound drug molecules are indicated. The interactions mediated by side chain and main chain atoms are depicted as solid and dashed lines, respectively. The interactions between drugs and DNA are indicated by dark red lines. Water molecules are depicted as "O". Interactions identical to those depicted in FIG. 3A are omitted from FIGS. 3B-3D. To simplify the presentation and avoid duplicating information, interactions between the protein and DNA backbones are indicated only for the bottom strand, whereas interactions between the protein and DNA bases are indicated only for the top strand.

Figure 4:
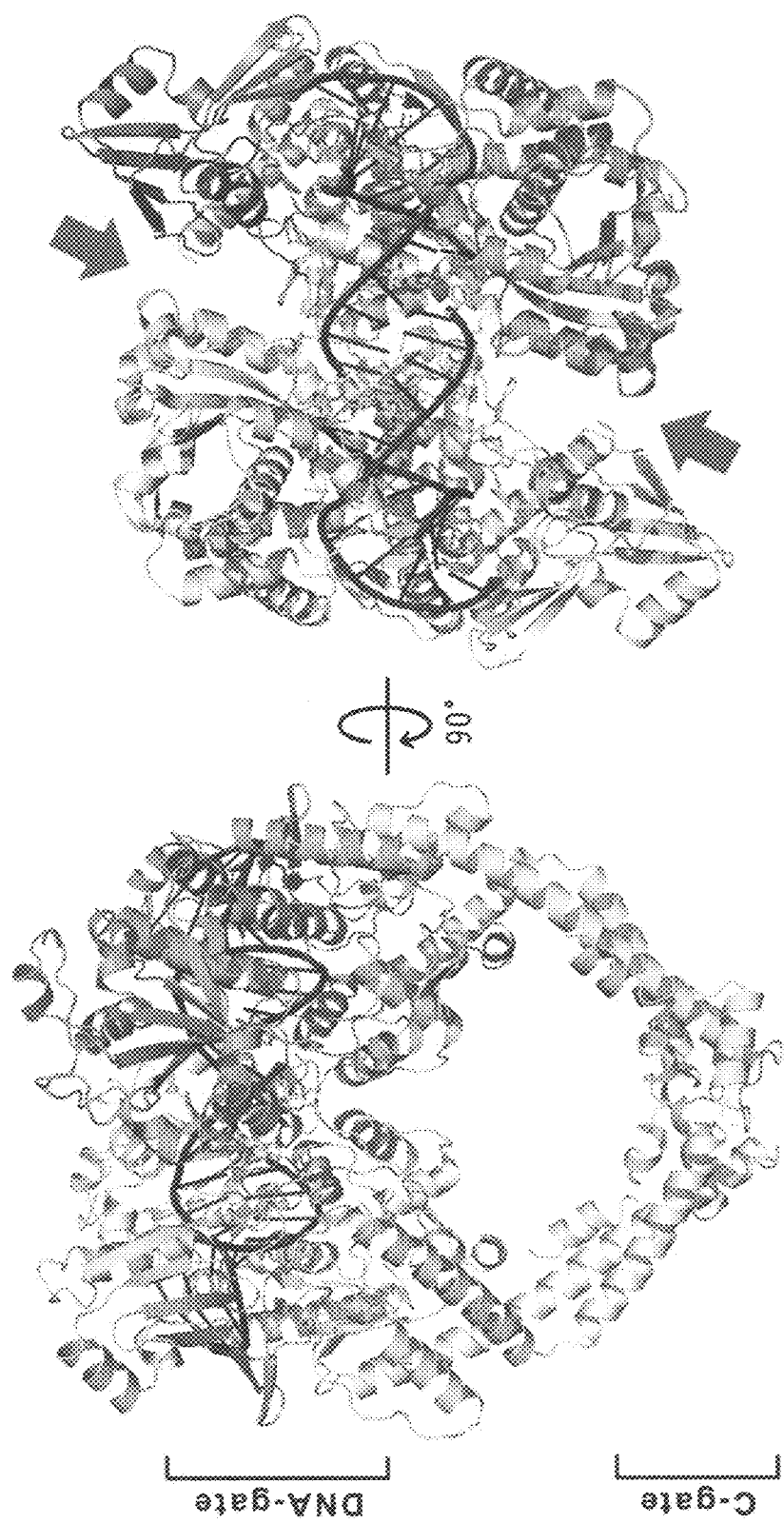
FIG. 4 depicts the structure of the hTOPIIβ$^{core}$-DNA-etoposide ternary complex, where DNA is in blue, one hTOPIIβ protomer is in gray and the other is colored to illustrate TOPRIM (green), WHO (pink), TOWER (orange) and C-gate (yellow) domains of the hTOPIIβ protomer.

FIG. 4 depicts the structure of the hTOPIIβ$^{core}$-DNA-etoposide ternary complex, where DNA is in blue, one hTOPIIβ protomer is in gray and the other is colored to illustrate TOPRIM (green), WHD (pink), TOWER (orange) and C-gate (yellow) domains of the hTOPIIβ protomer. Red arrowheads point to the gap between the TOPRIM and the tower domain. As illustrated in FIG. 4, one DNA duplex is enclosed symmetrically by the dimeric hTOPIIβ protomer.

Figure 5A:
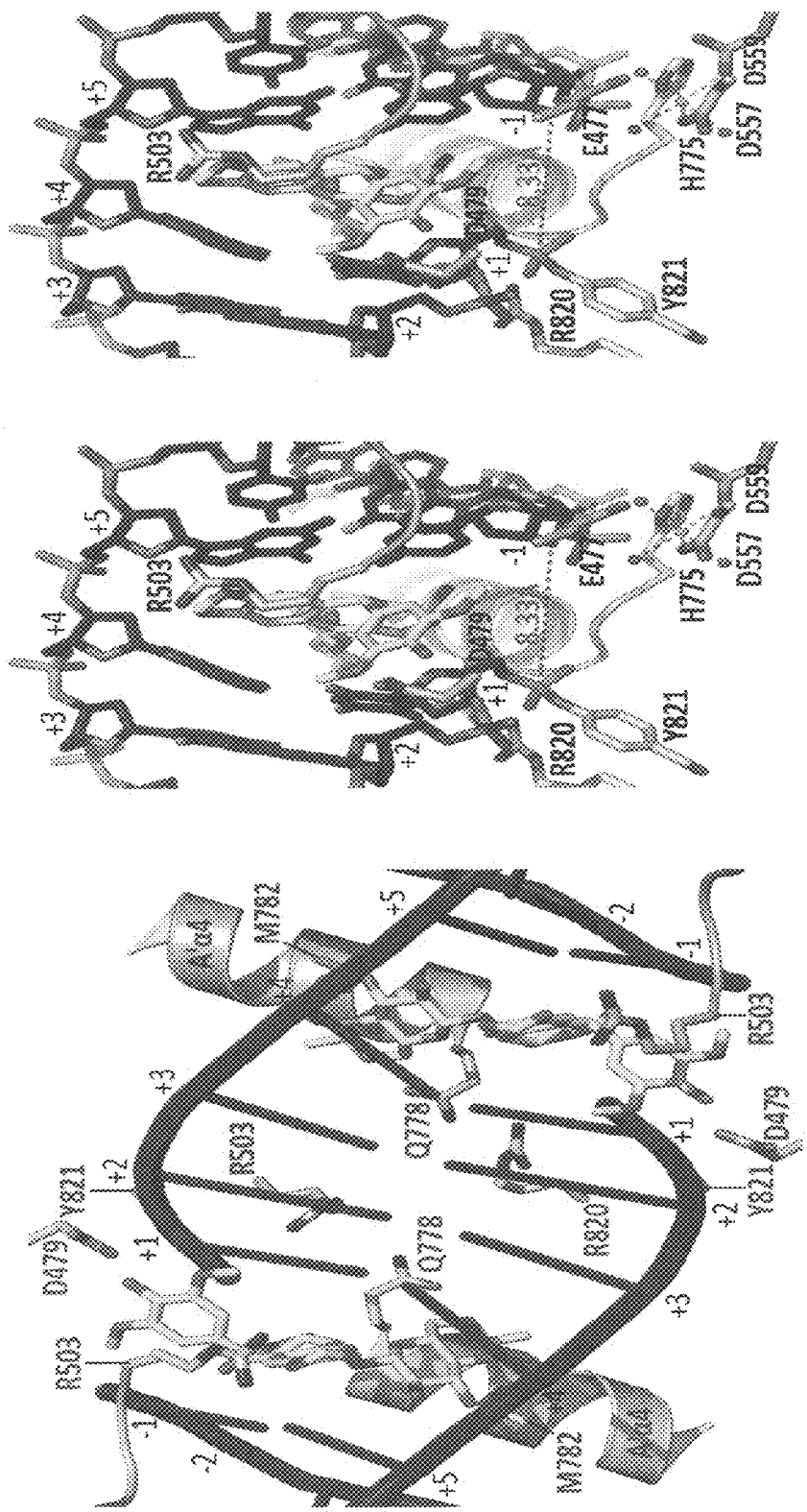
FIGS. 5A-5C illustrate detailed views of the drug-binding sites of the three ternary complexes: hTOPIIβ$^{core}$-DNA-etoposide (FIG. 5A), hTOPIIβ$^{core}$-DNA-mitoxantrone (FIG. 5B), and hTOPIIβ$^{core}$-DNA-doxorubicin (FIG. 5C)
Figure 5B:
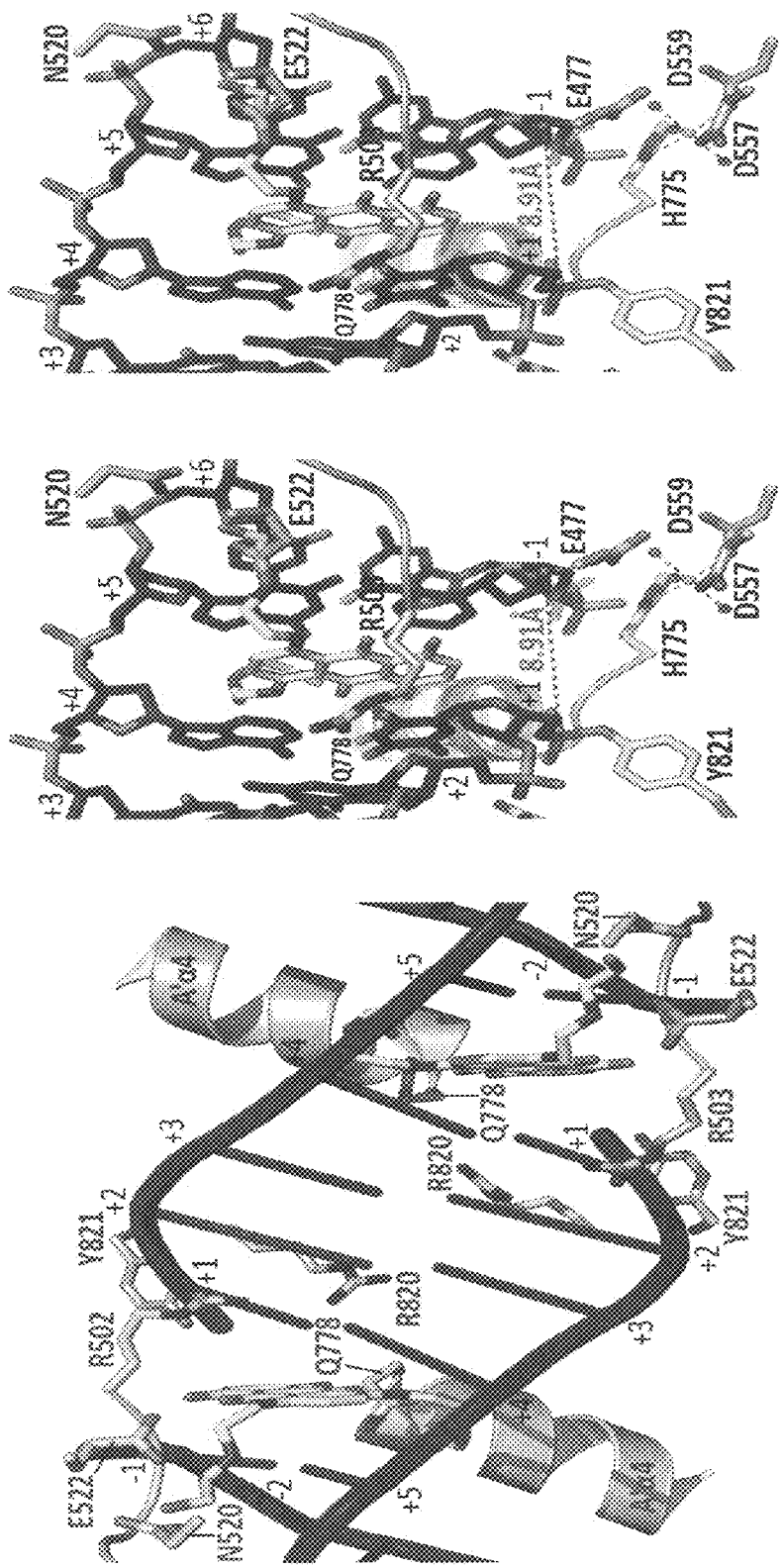
Figure 5C:
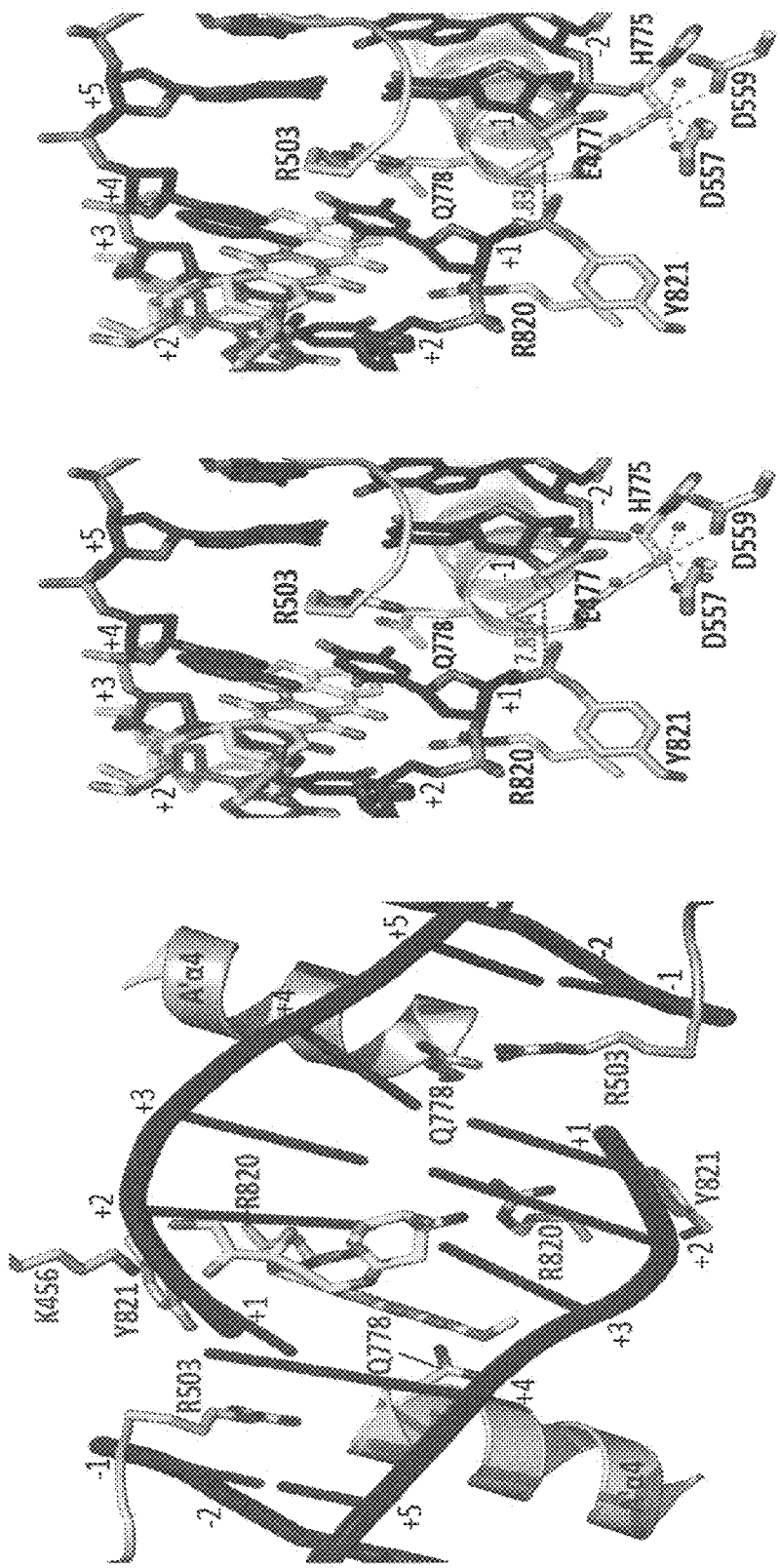
Figure 5D:
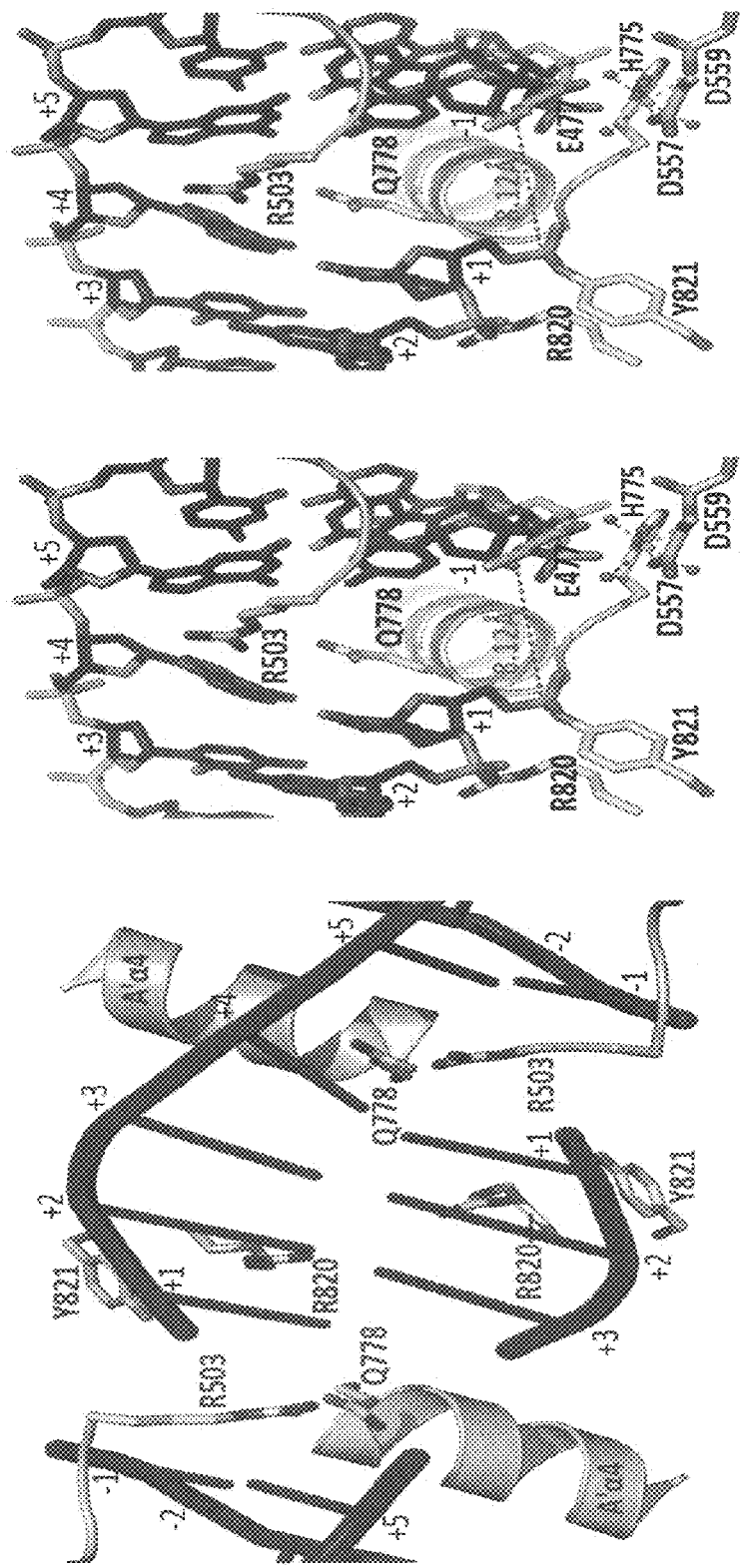
FIG. 5D illustrates detailed view of the cleavage sites of the drug-free hTOPIIβ$^{core}$-DNA binary complex.

Detailed views of the drug-binding sites of the three ternary complexes are illustrated in FIGS. 5A-5C. Cartoon/stick (left) and close-up stereo (right) representations show the targeting sites of etoposide (FIG. 5A), mitoxantrone (FIG. 5B), and doxorubicin (FIG. 5C), in which DNA is depicted in blue and the two hTOPIIβ protomers are colored differently. Mg$^{2+}$ and water molecules are depicted as green and red spheres, respectively. The distances between the Tyr821- linked scissile phosphate and the 3'-OH are indicated. FIG. 5D illustrates the cleavage sites of the hTOPIIβ$^{core}$-DNA binary complex. Note the insertion of residues Arg503 and Gln778 into the cleavage sites. Chemical structures of etoposide, mitoxantrone, amsacrine and doxorubicin are illustrated in FIG. 5E; drug-interacting residues are indicated and the interactions mediated by side chain and main chain atoms are shown as solid and dashed lines, respectively.

Figure 5E:
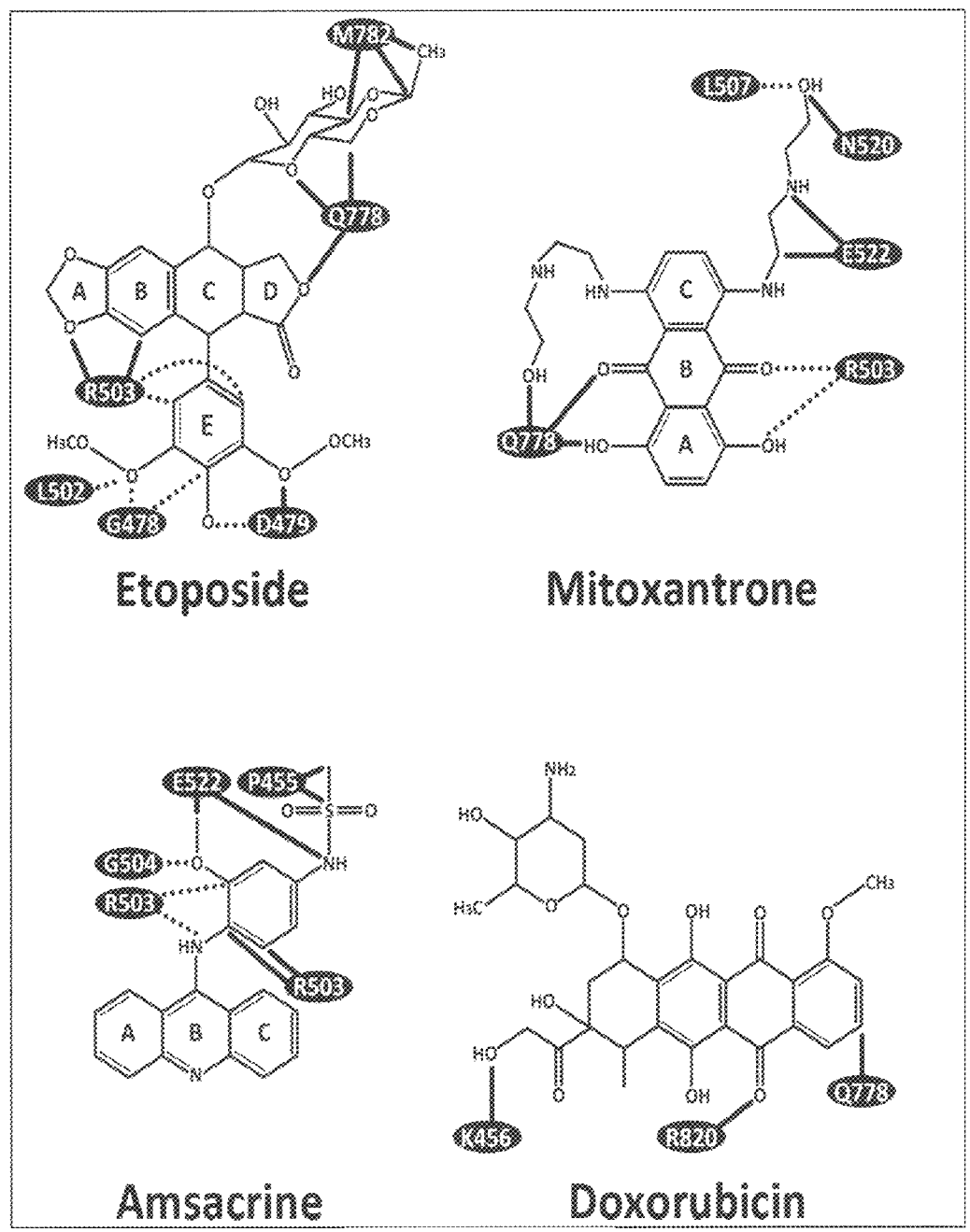
FIG. 5E depicts chemical structures of etoposide, mitoxantrone amsacrine and doxorubicin.

Reference is now made to FIGS. 4, 5A and 5E. The two etoposide molecules bind between the base pairs (+1/+4; −1/+5) immediately flanking the two cleaved scissile phosphates (FIG. 5A), with the drug's polycyclic aglycone core (rings A-D) sitting between base pairs and the glycosidic group and the E-ring protruding toward the DNA major and minor grooves, respectively. Unlike common DNA intercalators that stack against base pairs on both sides (B. A. Neto, A. A. lapis, *Molecules* 14, 1725 (2009)), the aglycone moiety stacks only with the −1/+5 base pair due to pronounced buckling of the +1/+4 base pair. The bound etoposide interacts extensively with both protein and DNA, involving many amino acid residues, the two base pairs at the cleavage site, and several neighboring deoxyribose rings (FIGS. 5A and 5E). Residues Asp479, Arg503, and Gln778 are notable for contacting both etoposide and DNA, and mutations at residues corresponding to Arg503 in eukaryotic TOPIIs confer drug resistance (Y. S. Vassetzky, G. C. Alghisi, S. M. Gasser, *Bioessays* 17, 767 (September, 1995)). The active involvement of hTOPIIβ in stabilizing the bound etoposide explains why the drug displays low affinity toward free DNA and is a poor DNA intercalation. The insertion of etoposide abolishes the stacking interaction between the +1/+4 and −1/+5 base pairs, which effectively blocks religation of the cleaved phosphodiester bond by keeping the 3'-OH approximately 8 Å away from the enzyme-linked 5'-phosphate group (FIG. 5A). In addition, the nucleophilicity of the 3'-OH is reduced by being detached from the catalytic $Mg^{2+}$ (B. H. Schmidt, A. B. Burgin, J. E. Deweese, N. Osheroff, J. M. Berger, *Nature* 465, 641 (Jun. 3, 2010)) due to structural changes in the active site. Together, these findings strongly suggest that etoposide stabilizes the cleavage complex by inhibiting the religation step.

Referring to FIGS. 5B and 5E. The mitoxantrone-bound structure reveals two drug molecules inserted four base pairs apart at the two cleavage sites once occupied by etoposide (FIG. 5B). However, unlike etoposide, the intercalation of mitoxantrone produces no buckling on the +1/+4 base pair, and the aromatic dihydroxyanthraquinone moiety (rings A-C) stacks with both flanking base pairs. The two alkylamino arms project toward the major and minor grooves, respectively, and embrace the +5 cytosine base from both sides while forming few interactions with the protein (FIG. 5E). In contrast to the extensive protein-mediated interactions that anchor etoposide, the bound mitoxantrone is largely stabilized by being sandwiched between base pairs. Although the Arg503 side chain adopts a new conformation, it remains a key drug-interacting residue because it contacts both mitoxantrone and DNA (FIG. 5B). The disposition of the cleaved DNA ends suggests that mitoxantrone and etoposide most likely share a common inhibitory mechanism of blocking the religation step via insertion into the cleavage sites.

Attention is now directed to FIGS. 5C and 5E. The binding mode of doxorubicin differs drastically from that seen for etoposide and mitoxantrone. Rather than binding to both cleavage sites, a single doxorubicin molecule binds asymmetrically within the four-base stagger between the two cleavage sites (FIG. 5C), which disrupts the usually highly preserved 2-fold symmetry associated with TOPII structures. The aglycone moiety (rings A-D) of this single doxorubicin molecule intercalates between the +1/+4 and +2/+3 base pairs and adopts a skewed orientation relative to the two phosphoribosyl backbones while the amino sugar and hydroxymethyl ketone moieties rest in the minor groove. Because there are very few protein-mediated contacts, the drug's conformation is stabilized mainly by its interactions with DNA (FIGS. 5C and 5E). Notably, instead of being sandwiched between two Watson-Crick base pairs, the doxorubicin molecule stacks against a Watson-Crick base pair (+2/+3) on one side and a reverse Hoogsteen base pair (+1/+4) on the other. A large repositioning of the +4 adenine base accompanied by a change in ribose ring-puckering likely favors the formation of this non-canonical base pair.

The preference for having the amino sugar and hydroxymethyl ketone groups located in the minor groove, as seen in the structures of doxorubicin-DNA binary complexes, may explain why doxorubicin does not bind at the cleavage site where the minor groove is approached by TOPII, which leaves little space to accommodate the two appended drug moieties (FIG. 5C). The protrusion of the amino sugar moiety toward the distal cleavage site prevents the binding of a second doxorubicin molecule within the four-base stagger because the simultaneous presence of two drug molecules at both symmetry-related base pair steps would cause steric clashes between the two amino sugar groups. Despite the absence of drug molecules in the cleavage sites, the 3'-OH and enzyme-linked 5'-phosphate groups of the two cleaved phosphodiester bonds remain widely separated, with Arg503 inserted between the +1 and −1 bases. Therefore, unlike etoposide and mitoxantrone which block religation by directly entering the cleavage sites, doxorubicin prevents religation by binding asymmetrically to the four-base stagger. This asymmetrical binding misaligns the cleaved DNA ends by inducing the formation of a reverse Hoogsteen base pair. The insertion of Arg503 into the cleavage site may act in concert with doxorubicin to further repress religation. As described hereinabove, there are two distinct TOPII isozymes. The α-isoform is particularly important for DNA replication and is usually present at high levels in fast growing cells, including many types of tumors (C. Oakman, E. Moretti, C. Sotiriou, G. Viale, A. Di Leo, *J Natl Cancer Inst* 101, 1735 (Dec. 16, 2009)), whereas the β-isoform is mainly involved in transcription-related processes (B. G. Ju et al., *Science* 312, 1798 (Jun. 23, 2006)). Although the inhibition of both TOPII isoforms contributes to the drug-induced death of cancer cells, targeting of the β-isoform has been implicated in deleterious therapy-related side effects associated with chromosome rearrangements (A. M. Azarova et al., *Biochem Biophys Res Commun* 399, 66 (Aug. 13, 2010)). Thus, it is clinically desirable to have isoform-specific TOPII-targeting agents available. Although most drug-contacting residues are conserved between the two isoforms, we noted that a key drug-interacting residue Gln778 (FIG. 5E) is replaced with methionine in the α-isoform. Such a change in residue polarity may be exploitable in developing new antitumor drugs with the desired isozyme specificity.

Figure 6A:
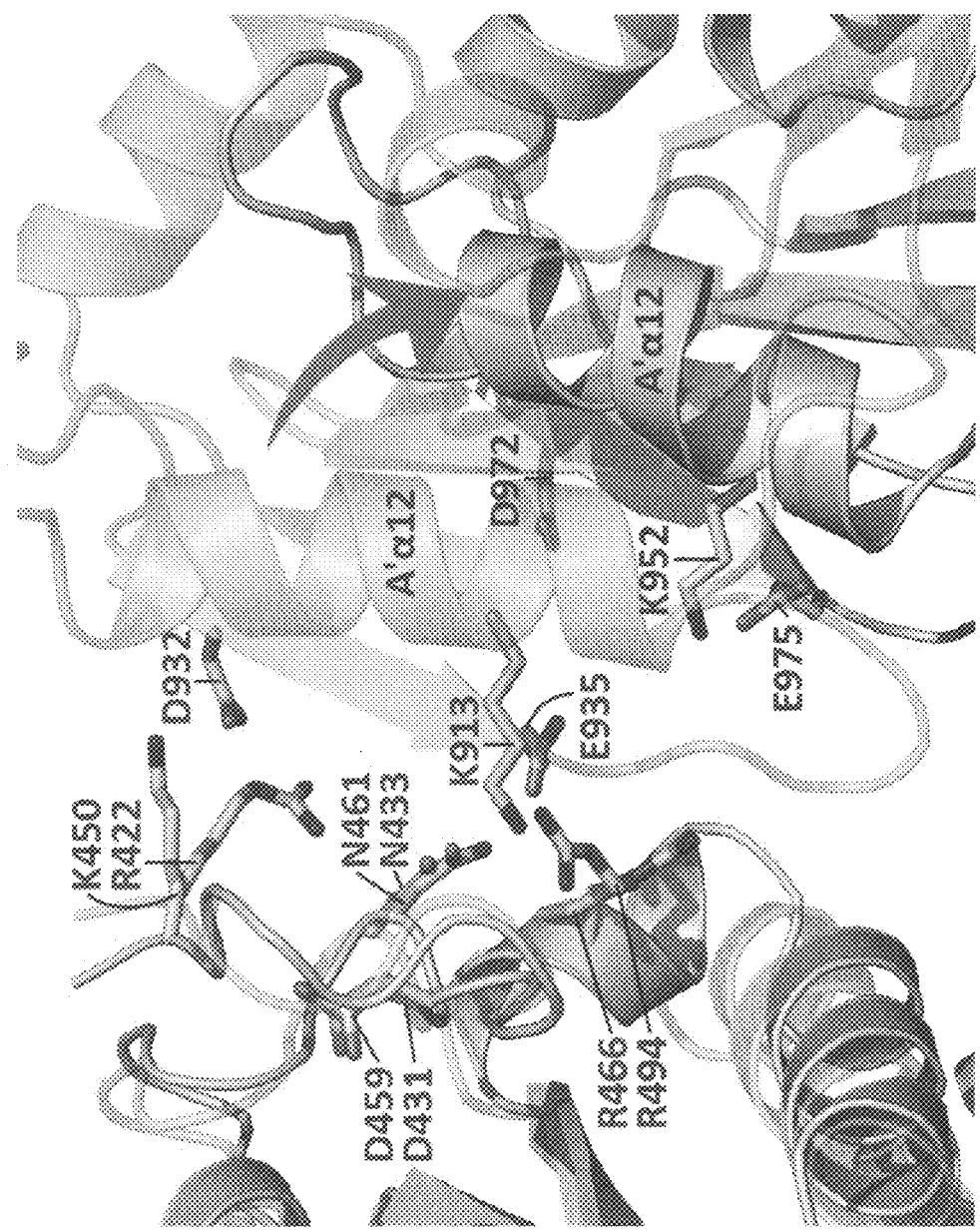
FIG. 6A depicts relative orientations between the TOPRIM and tower domains by superimposing the TOPRIM domains from drug-free hTOPIIβ$^{core}$-DNA binary complex (pink) and yeast TOPII (cyan; PDBid: 3I4K; a TOPII$^{core}$-DNA binary complex) structures.
Figure 6B:
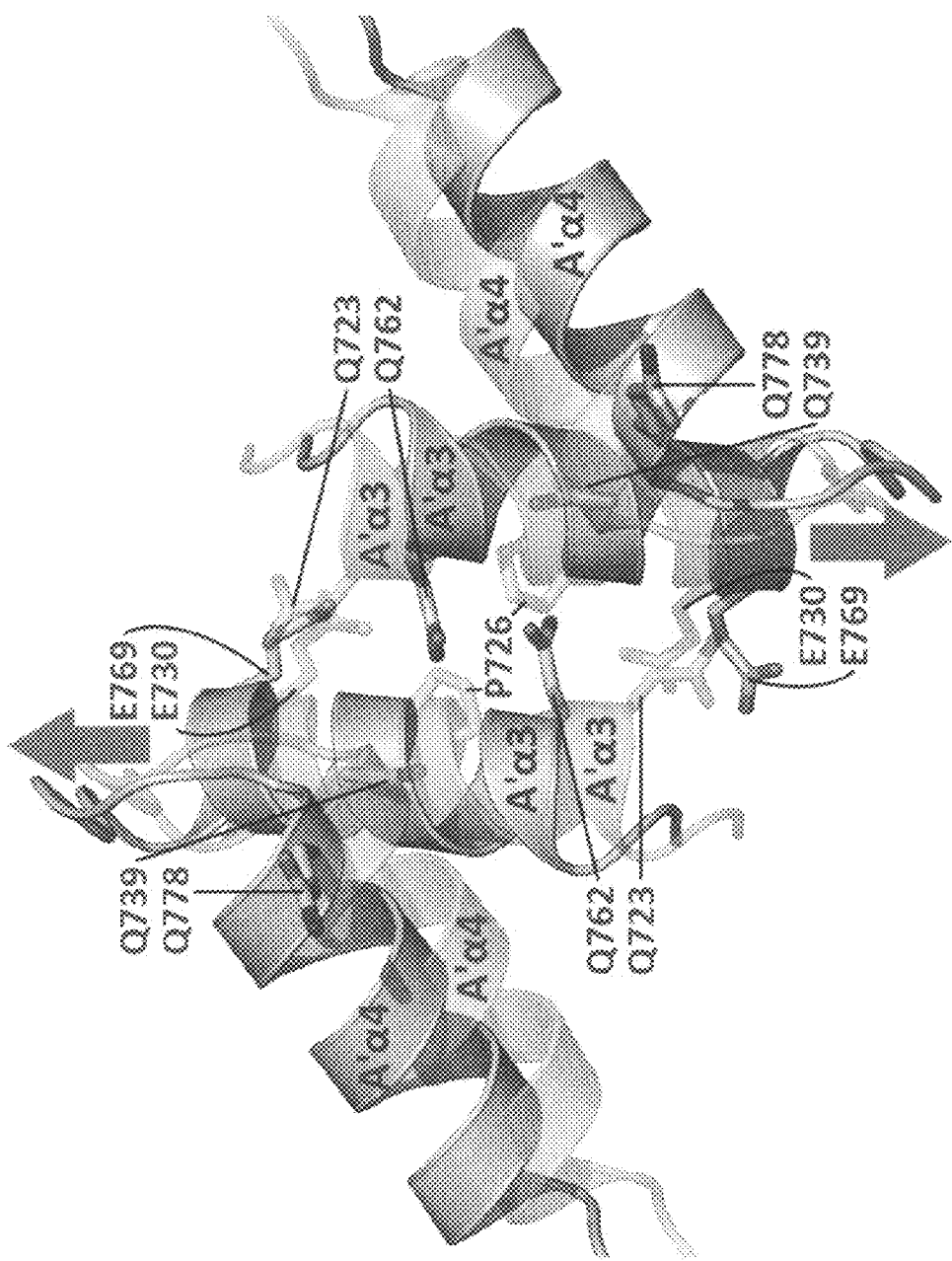
FIG. 6B illustrates the change in the packing between the two WHD domains in hTOPIIβ and yeast TOPII structures by sliding the two A'α3 helices about the structural dyad.

In the three drug-bound ternary structures reported here, the hTOPIIβ adopts a more open quaternary structure than in other DNA-bound structures reported for bacterial and yeast TOPII, with no interactions observed between the TOPRIM domain of one protomer and the tower domain of the other (FIG. 4). As illustrated in FIG. 6A, superimposing the TOPRIM domains from hTOPIIβ (pink; this work) and yeast TOPII (cyan; PDBid 3L4K; a TOPII-DNA binary complex) shows that the relative orientations between the TOPRIM and tower domains are different in these two structures. Moreover, sliding of the two A'α3 helices about the structural dyad changes the packing between the two WHD domains in hTOPIIβ and yeast TOPII (FIG. 6B). In FIG. 6C, side chain conformations exhibit by residues Arg503 and Gln778 in the drug-free hTOPIIβ and yeast TOPII are different. Insertion of residues Arg503 and Gln778 into the cleavage sites was observed in drug-free hTOPIIβ. Therefore, these structures represent a newly observed quaternary conformation of DNA-bound TOPII.

Removal of the pre-bound drug molecule did not result in religation, indicating that this new quaternary conformation may represent a stable structural state of the TOPII cleavage complex. The rearrangement of residues flanking the cleavage site, as observed in the drug-free hTOPIIβ-DNA binary structure, also reveals crucial new insights into how a TOPII cleavage complex undergoes conformational change from a closed post-cleavage state, as seen in the yeast and bacterial TOPII structures, to an open form with widely separated DNA ends that is required for strand passage.

Specifically, we noted the insertion of the Arg503 and Gln778 side chains directly into the cleavage site between the +1/+4 and −1/+5 base pairs (FIGS. 5D and 6C), which appears to stabilize the cleaved state by interfering with the re-stacking of these adjacent base pairs and the nucleophilic attack of the 3'-OH on the phosphotyrosyl bond. Consistent with the proposed involvement of Arg503 in TOPII catalysis, mutation of this residue impairs the enzyme's decatenation activity (I. Laponogov et al., *PLoS One* 5, e11338 (2010)).

Additionally, in the TOPIIβ-DNA binary structure, the distances between the 3' ends of the two cleavage sites and between the two DNA-intercalating isoleucine residues (ile872) is longer than those observed for the closed structures (Table 3); therefore, our structure is likely to represent an initial transition toward the open conformation.

Figure 7A:
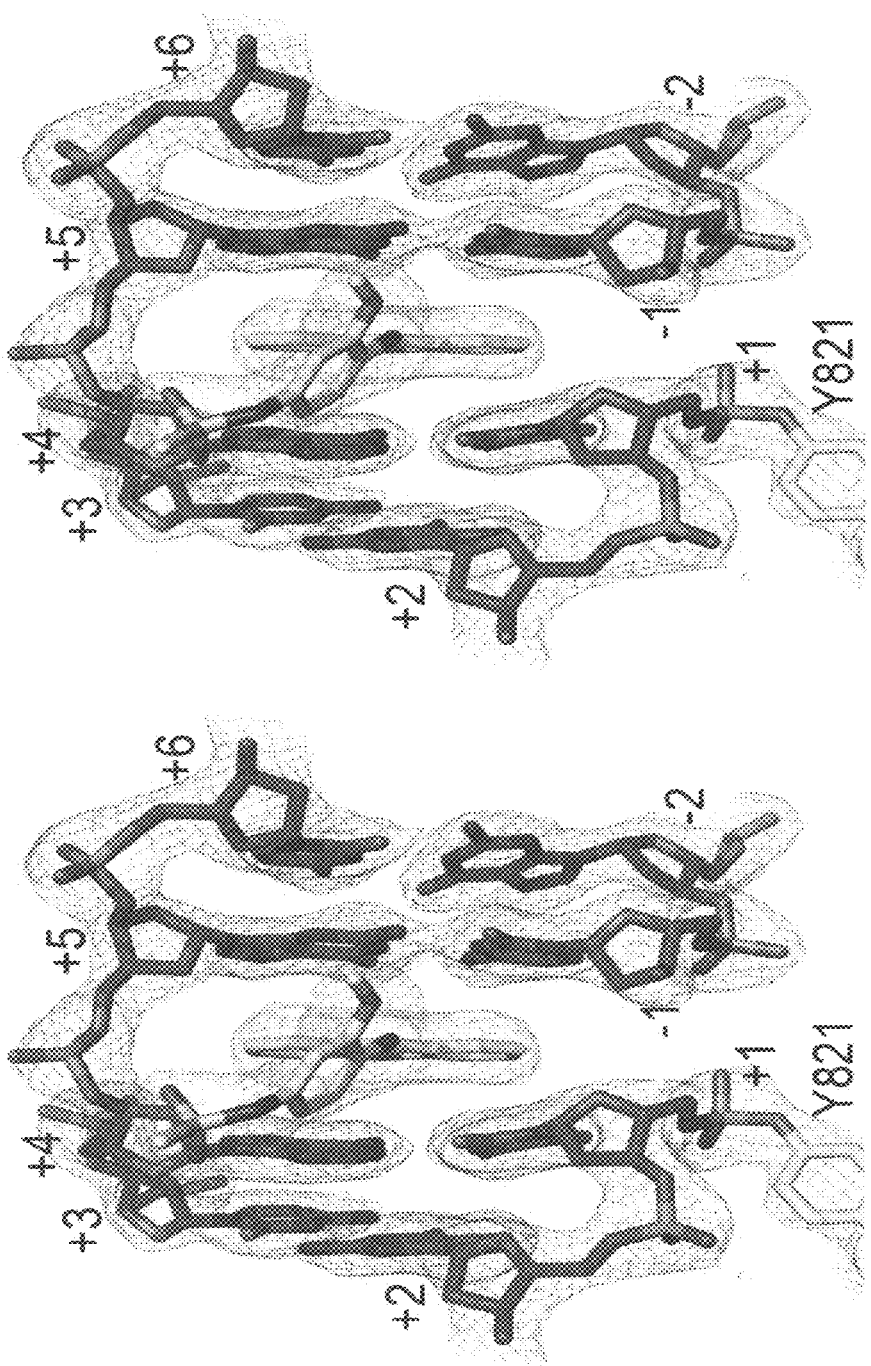
FIGS. 7A and 7B depict the electron density maps of the bound mAMSA in the hTOPIIβ$^{core}$-DNA-mAMSA ternary complex.
Figure 7B:
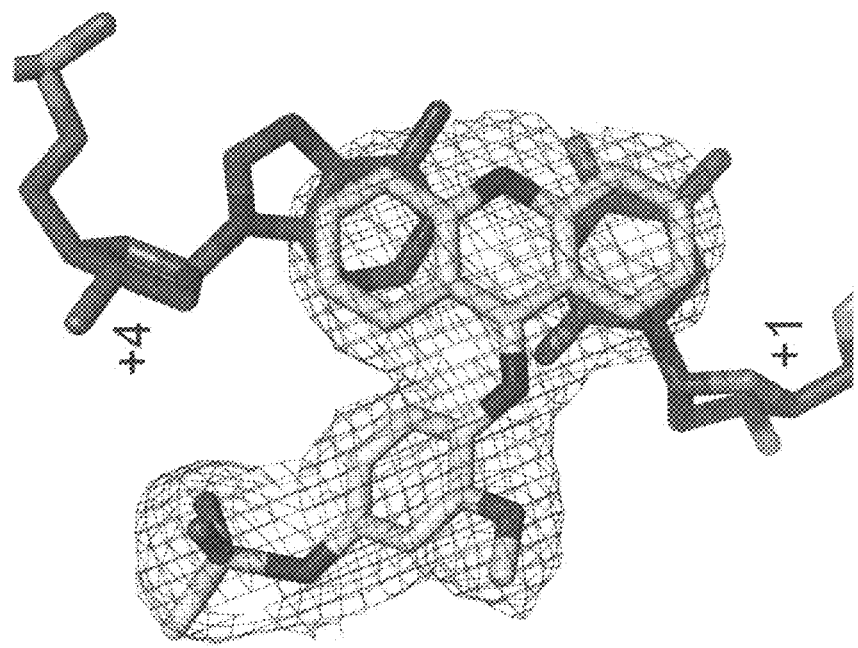
Figure 7B:
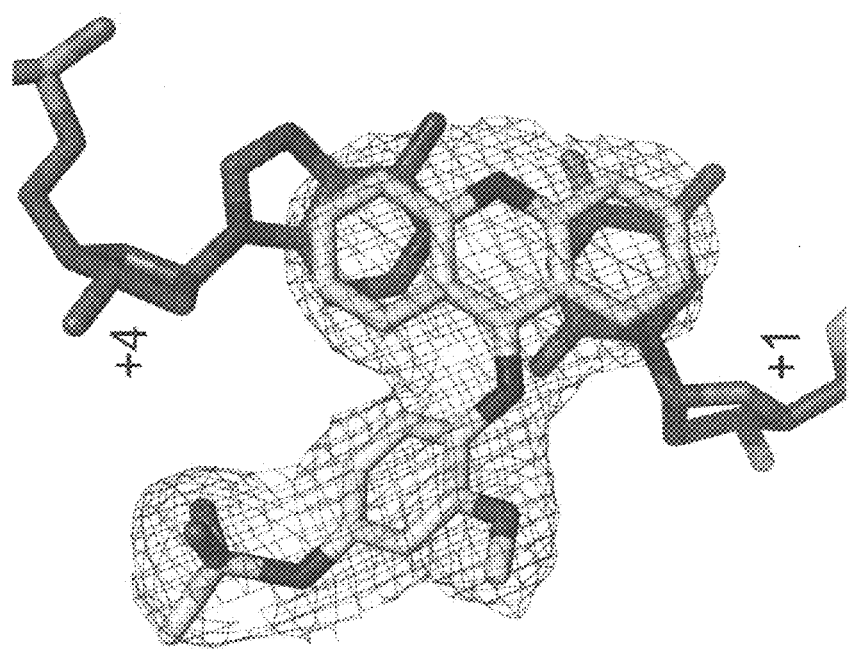

FIGS. 7A and 7B depict the electron density maps of the bound mAMSA in the hTOPIIβ$^{core}$-DNA-mAMSA ternary complex. Stereo representation of unbiased $F_o-F_c$ difference electron density maps of drug showing the presences of mAMSA. The $F_o-F_c$ difference electron density maps (contoured at 3.0σ) of drugs obtained by refinement using drug-free hTOPIIβ$^{core}$-DNA structure are shown in green meshes. The final 2 $F_o-F_c$ maps (contoured at 1.5σ) of selected DNA base pairs and +1 thymidine-conjugated Y821 are shown in blue meshes (FIG. 7A). Stereo representation of the final 2 $F_o-F_c$ maps of bound mAMSA. The 2 $F_o-F_c$ maps (contoured at 1.0σ) of drugs are shown in blue meshes (FIG. 7B).

Figures 8A, 8B, 8C:
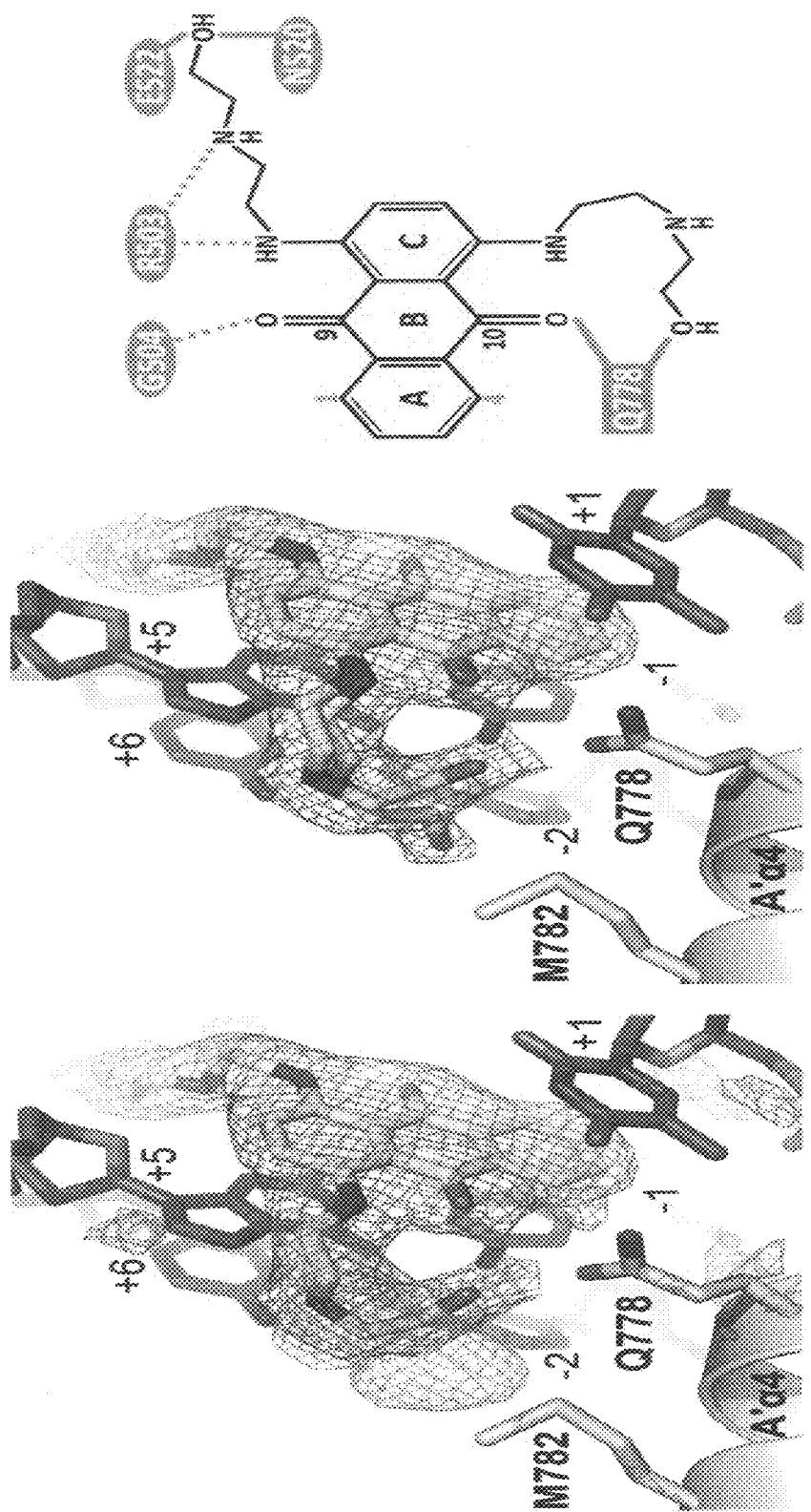
FIGS. 8A-8E illustrate that ametantrone displays extremely similar binding mode of mitoxantrone but has fewer direct interactions with hTOPIIβ.
Figure 8E:
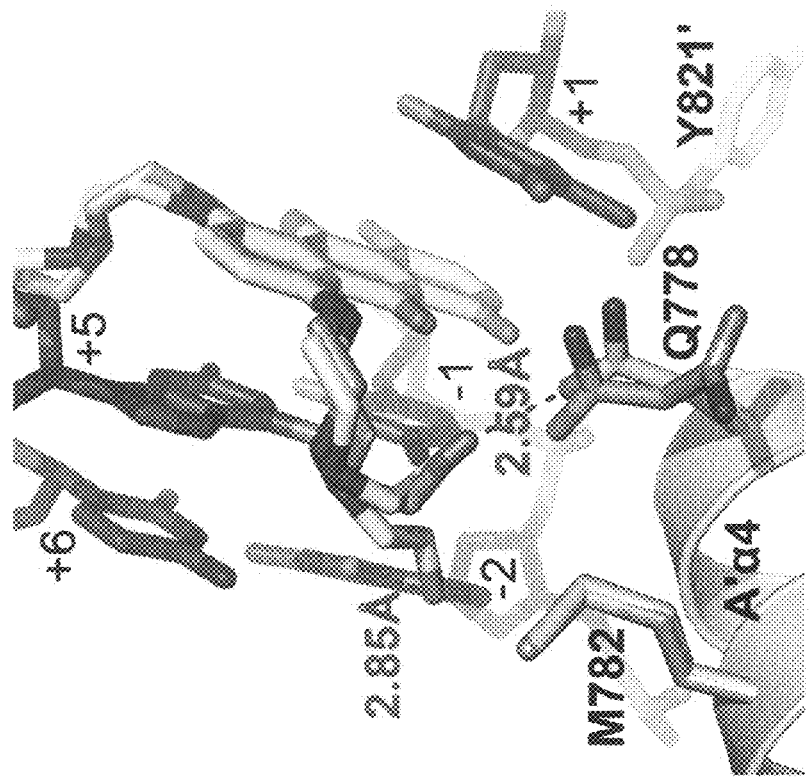
Figure 8D:
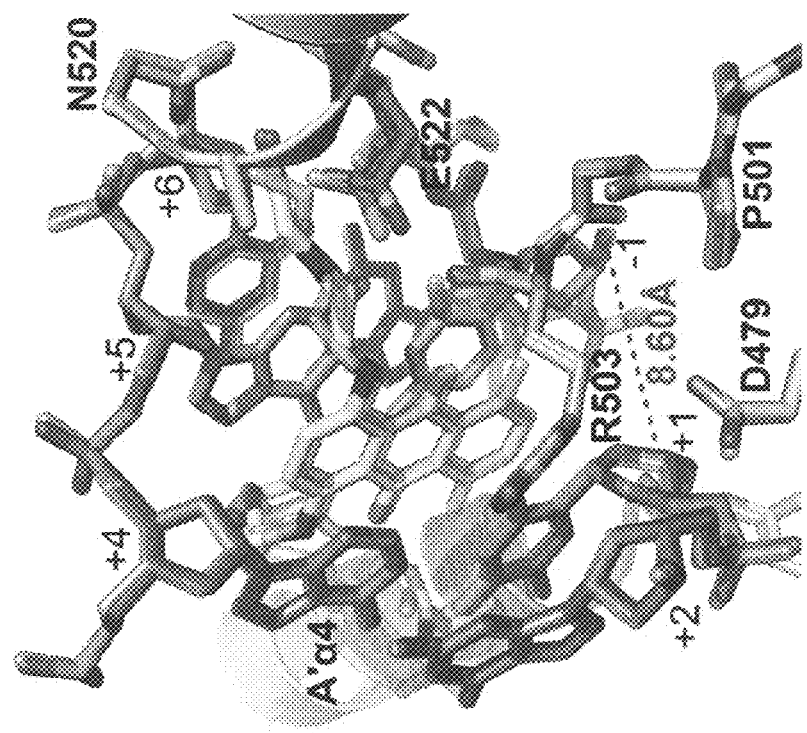

Referring to FIGS. 8A-8E, compared with mitoxantrone, ametantrone displays extremely similar binding mode but has fewer direct interactions with hTOPIIβ and DNA. The 2 $F_o-F_c$ (blue meshes; contoured at 1.0σ) and unbiased Fo-Fc (green meshes; contoured at 3.0σ) electron density maps of the bound ametantrone. The strong positive peak in $F_o-F_c$ difference map at major groove-binding pocket indicates the presence of dual conformations for one alkylamino arm (FIG. 8A). The 2 $F_o-F_c$ electron density maps (blue meshes; contoured at 1.0σ) of the bound ametantrone after building the second conformer of its major groove-locating alkylamino arm (FIG. 8B). Chemical structure of ametantrone with the drug-contacting residues indicated. The interactions mediated by side-chain and main-chain atoms are shown as green solid and dashed lines, respectively. Atoms involve in drug-DNA interactions are shaded gray (FIG. 8C). Moreover, referring to FIGS. 8D-8E, superposition of hTOPIIβ$^{core}$-DNA-mitoxantrone (grey) and hTOPIIβ$^{core}$-DNA-ametantrone (in CPK color) ternary complexes shows structural differences of minor groove- and major groove-binding pockets, respectively. DNA bases of hTOPIIβ$^{core}$-DNA-ametantrone ternary complexes are shown in purple stick, and protein is shown in cartoon/stick representation and the two hTOPIIβ monomers are respectively colored in pink and yellow. Labels belonging to the second monomer are flagged by a prime. Distance between the Y821'-linked scissile phosphate and the 3'-OH of ametantrone-bound structure is indicated in panel D. Interactions between the dual terminal hydroxyl groups of alkylamino arm of ametantrone and protein are indicated in panel E.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements.

TABLE 3

Distances between selected groups in TOPII-DNA complexes[a]

| | Distance (Å) | | | |
|---|---|---|---|---|
| Structure | Active site Tyr→Tyr | Cleavage site 5'-P→3'-OH | Cleavage site 3'-OH→3'-OH | DNA-intercalating ile→ile |
| hTOPIIβ structures (present disclosure) | ~18.53 | ~8.25 | ~31.77 | ~52.77 |
| 3L4K[b] (*S. cerevisea*) | 23.63 | — | 29.74 | 47.71 |
| 2XCS[c] (*S. aureua* DNA Gyrase) | 23.82 | — | — | 48.89 |
| 3LTN[d] | 21.38 | 5.87 | 30.70 | 49.17 |
| 3KSA[d] | 23.78 | 4.89 | 30.34 | 48.33 |
| 3KSB[d] (*S. pneumoniae*) | 24.64 | — | — | 48.35 |

[a]The reported values for hTOPIIβ were averaged using all four structures reported in this study. Note that the 3L4K model has no 5'-P at the cleavage site, and the 2XCS and 3KSB models have no double-strand breaks.
[b]B. H. Schmidt, A. B. Burgin, J. E. Deweese, N. Osheroff, J. M. Berger, *Nature* 465, 641 (Jun. 3, 2010).
[c]B. D. Bax et al., *Nature* 466, 935 (Aug. 19, 2010).
[d]I. Laponogov et al., *PLoS* One 5, e11338 (2010).

It will be understood that the above description of embodiments is given by way of example only and that various modifications may be made by those to with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A crystal of an hTOPII$^{core}$-DNA binary complex comprising:
   an hTOPII portion comprising an hTOPII core domain (hTOPII$^{core}$); and
   a synthetic double-stranded DNA, which is in complex with the hTOPII portion,
   wherein the synthetic double-stranded DNA comprises:
   a first DNA strand corresponding to nucleotide positions 3 to 20 of the sequence of 5'-NNNC-CGAGCNNNNGCTCGGNNN-3' (SEQ ID NO: 1), wherein N is any one of adenine, thymine, cytosine or guanine; and
   a second DNA strand that is complementary to the first DNA strand.

2. The crystal of claim 1, wherein:
   the hTOPII is hTOPTIIα; and
   the first DNA strand has a sequence from 5' to 3', AGC-CGAGCTGCAGCTCGGCT (SEQ ID NO: 3).

3. The crystal of claim 1, wherein:
   the hTOPII is hTOPIIβ; and
   the first DNA strand has a sequence from 5' to 3', AGC-CGAGCTGCAGCTCGGCT (SEQ ID NO: 3).

4. The crystal of claim 3, wherein the crystal has a crystal lattice in a P2$_1$ space group and unit cell dimensions of a=80.0±2 Å, b=176.4±3 Å, c=94.2±2 Å, and β=112.1±3 degree.

5. A method for preparing a crystal of an hTOPII$^{core}$-DNA binary complex comprising the steps of:
   (a) mixing an hTOPII portion comprising an hTOPII core domain, a synthetic double-stranded DNA, and a ligand to form an hTOPII$^{core}$-DNA-ligand ternary complex;
   (b) mixing the hTOPII$^{core}$-DNA-ligand ternary complex with a first solution to crystallize the hTOPII$^{core}$-DNA-ligand ternary complex; and
   (c) placing the crystallized hTOPII$^{core}$-DNA-ligand ternary complex in a second solution to soak out the ligand from the crystallized hTOPII$^{core}$-DNA-ligand ternary complex, thereby obtaining the crystal of the hTOPII$^{core}$-DNA binary complex,
   wherein the synthetic double-stranded DNA comprises:
   a first DNA strand corresponding to nucleotide positions 3 to 20 of the sequence of 5'-NNNC-CGAGCNNNNGCTCGGNNN-3' (SEQ ID NO: 1), wherein N is any one of adenine, thymine, cytosine or guanine; and
   a second DNA strand that is complementary to the first DNA strand.

6. The method of claim 5, wherein:
   the hTOPII is hTOPIIα;
   the first DNA strand has a sequence from 5' to 3', AGC-CGAGCTGCAGCTCGGCT (SEQ ID NO: 3); and
   the ligand is mitoxantrone.

7. The method of claim 6, wherein in the step (a), the synthetic double-stranded DNA is mixed with the hTOPIIα portion in a molar ratio of about 1:1 to 1.5:1.

8. The method of claim 6, wherein the first solution in the step (b) comprises 100 mM magnesium acetate, 50 mM 2-(N-morpholino)ethanesulfonic acid (pH 5.2-6.0), and 20-27 wt % 2-methyl-1,6-hexanediol (MPD).

9. The method of claim 6, wherein the second solution in the step (c) comprises 100 mM magnesium acetate, 50 mM 2-(N-morpholino)ethanesulfonic acid (pH 5.2-6.0), and 30-40 wt % 2-methyl-1,6-hexanediol (MPD).

10. The method of claim 5, wherein:
the hTOPII is hTOPIIβ;
the first DNA strand has a sequence from 5' to 3', AGC-CGAGCTGCAGCTCGGCT (SEQ ID NO: 3); and
the ligand is etoposide.

11. The method of claim 10, wherein in the step (a), the synthetic double-stranded DNA is mixed with the hTOPIIβ portion in a molar ratio of about 1:1 to 1.5:1.

12. The method of claim 10, wherein the first solution in the step (b) comprises 100 mM magnesium acetate, 50 mM 2-(N-morpholino)ethanesulfonic acid (pH 5.6-6.5), and 18-22 wt % 2-methyl-1,6-hexanediol (MPD).

13. The method of claim 10, wherein the second solution in the step (c) comprises 100 mM magnesium acetate, 50 mM 2-(N-morpholino)ethanesulfonic acid (pH 5.6-6.5), and 22-40 wt % 2-methyl-1,6-hexanediol (MPD).

14. A crystal of an hTOPII$^{core}$-DNA-ligand ternary complex comprising:
an hTOPII portion comprising an hTOPII core domain; and
a synthetic double-stranded DNA and a ligand, which are in complex with the hTOPII portion,
wherein the synthetic double-stranded DNA comprises:
a first DNA strand corresponding to nucleotide positions 3 to 20 of the sequence of 5'-NNNC-CGAGCNNNNGCTCGGNNN-3' (SEQ ID NO: 1), wherein N is any one of adenine, thymine, cytosine or guanine; and
a second DNA strand that is complementary to the first DNA strand.

15. The crystal of claim 14, wherein the
the hTOPII is hTOPIIα; and
the first DNA strand has a sequence from 5' to 3', AGC-CGAGCTGCAGCTCGGCT (SEQ ID NO: 3).

16. The crystal of claim 15, wherein the ligand is mitoxantrone.

17. The crystal of claim 16, wherein the crystal has a crystal lattice in a P2$_1$22$_1$ space group and unit cell dimensions of a=105.4±2 Å, b=126.2±3 Å, and c=198.0±2 Å.

18. The crystal of claim 14, wherein the
the hTOPII is hTOPIIβ; and
the first DNA strand has a sequence from 5' to 3', AGC-CGAGCTGCAGCTCGGCT (SEQ ID NO: 3).

19. The crystal of claim 18, wherein the ligand is etoposide.

20. The crystal of claim 19, wherein the crystal has a crystal lattice in a P2$_1$ space group and unit cell dimensions of a=80.2±2 Å, b=176.8±3 Å, c=94.0±2 Å, and β=111.6±3 degree.

21. The crystal of claim 18, wherein the ligand is mitoxantrone.

22. The crystal of claim 21, wherein the crystal has a crystal lattice in a P2$_1$ space group and unit cell dimensions of a=80.5±2 Å, b=176.6±3 Å, c=93.8±2 Å, and β=111.5±3 degree.

23. The crystal of claim 18, wherein the ligand is doxorubicin.

24. The crystal of claim 23, wherein the crystal has a crystal lattice in a P2$_1$ space group and unit cell dimensions of a=80.3±2 Å, b=176.6±3 Å, c=94.0±3 Å, and β=111.5±3 degree.

25. The crystal of claim 18, wherein the ligand is amsacrine.

26. The crystal of claim 25, wherein the crystal has a crystal lattice in a P2$_1$ space group and unit cell dimensions of a=80.2±2 Å, b=176.8±3 Å, c=94.0+3 Å, and β=111.6±3 degree.

27. The crystal of claim 18, wherein the ligand is ametantrone.

28. The crystal of claim 27, wherein the crystal has a crystal lattice in a P2$_1$ space group and unit cell dimensions of a=80.2±2 Å, b=176.8±3 Å, c=94.0±3 Å, and β=111.6±3 degree.

29. A high throughput screening method for identifying a ligand exhibiting inhibitory effect toward hTOPII comprising steps of:
(a) soaking a ligand into the crystal of the hTOPII$^{core}$-DNA binary complex of claim 8 to form an hTOPII$^{core}$-DNA-ligand ternary complex;
(b) obtaining an X-ray crystal diffraction pattern of the hTOPII$^{core}$-DNA-ligand ternary complex; and
(c) using the X-ray crystal diffraction pattern to analyze the structure of hTOPII$^{core}$-DNA-ligand ternary complex, and to identify ligand-interacting residues on hTOPII,
wherein the ligand comprises a hTOPII-targeting agent.

30. The high throughput screening method of claim 29, wherein the hTOPII is hTOPIIα.

31. The high throughput screening method of claim 30, wherein the first DNA strand has a sequence from 5' to 3', GCCGAGCTGCAGCTCGGC (SEQ ID NO: 2).

32. The high throughput screening method of claim 30, wherein the first DNA strand has a sequence from 5' to 3', AGCCGAGCTGCAGCTCGGCT (SEQ ID NO: 3).

33. The high throughput screening method of claim 29, wherein the hTOPII is hTOPIIβ.

34. The high throughput screening method of claim 33, wherein the first DNA strand has a sequence from 5' to 3', GCCGAGCTGCAGCTCGGC (SEQ ID NO: 2).

35. The high throughput screening method of claim 33, wherein the first DNA strand has a sequence from 5' to 3', AGCCGAGCTGCAGCTCGGCT (SEQ ID NO: 3).

* * * * *